United States Patent [19]

Lau

[11] Patent Number: 5,049,358
[45] Date of Patent: Sep. 17, 1991

[54] COMPOSITION AND TEST DEVICE FOR ASSAYING FOR PROTEINS

[75] Inventor: Arthur L. Y. Lau, Granger, Ind.

[73] Assignee: Miles Inc., Elkhart, Ind.

[21] Appl. No.: 251,297

[22] Filed: Sep. 30, 1988

[51] Int. Cl.$^5$ .................... G01N 21/78; G01N 33/68
[52] U.S. Cl. .................................... 422/56; 436/86; 436/163; 436/169
[58] Field of Search .................. 436/86–88, 436/163, 169, 170; 422/56–58

[56] References Cited

U.S. PATENT DOCUMENTS

| | | | |
|---|---|---|---|
| 2,643,230 | 6/1953 | Mooradian et al. | 436/163 |
| 3,438,737 | 4/1969 | Atkinson et al. | 436/86 |
| 3,485,587 | 12/1969 | Keston | 436/86 |
| 3,592,603 | 7/1971 | Miller et al. | 436/163 X |
| 4,125,376 | 11/1978 | Razulis | 422/57 X |
| 4,149,852 | 4/1979 | Tiru et al. | 436/163 |
| 4,260,777 | 4/1981 | Rittersdorf et al. | 436/86 X |
| 4,287,153 | 9/1981 | Towsend | 422/56 |
| 4,376,827 | 3/1983 | Stiso et al. | 422/56 X |
| 4,511,660 | 4/1985 | Lubbers et al. | 436/163 |

FOREIGN PATENT DOCUMENTS 2132348  7/1984  United Kingdom .

Primary Examiner—Robert J. Hill, Jr.
Attorney, Agent, or Firm—Robert N. Coe

[57] ABSTRACT

A test device and method of determining the presence and concentration of proteins, such as albumin or Bence Jones proteins, in a test sample. The test device includes a carrier matrix incorporating a reactant system capable of interacting with proteins to produce a visually or instrumentally detectable and/or measurable response. The carrier matrix of the device can include commonly use bibulous matrices, such as filter paper, or a nonbibulous protein-permeable strip, membrane or layer of a polymerized urethane-containing composition. In addition, a reactant system, including a dual indicator reagent system, such as bromophenol blue, methyl orange and, if necessary, a suitable buffer, is incorporated into the carrier matrix to provide improved color resolution and increased sensitivity to proteins, thereby affording a more accurate and trustworthy protein assay of test samples, such as urine. Furthermore, by incorporating the dual indicator reagent system into a carrier matrix including a polymerized urethane-containing composition, a dry phase assay for low molecular weight proteins, such as Bence Jones proteins, can be performed on a liquid test sample.

21 Claims, 4 Drawing Sheets

COMPOSITION AND TEST DEVICE FOR ASSAYING FOR PROTEINS

FIELD OF THE INVENTION

The present invention relates to a device and a method of assaying a test sample for the presence and concentration of proteins. More particularly, the present invention relates to a new and improved method and device for assaying a liquid, such as urine, for proteins by utilizing a device having a dual indicator reagent composition as the reactant composition. The dual indicator reagent composition is incorporated into a carrier matrix, such that a detectable and/or measurable response occurs upon contact of the dual indicator reagent composition with a protein-containing test sample. The dual indicator reagent composition provides improved color resolution and increased protein sensitivity in order to more accurately detect and/or measure, either visually or by instrument, the protein content of a liquid test sample. In addition, the present invention relates to using a dual indicator reagent composition, incorporated into a carrier matrix comprising a protein-permeable strip, membrane or layer of a polymerized urethane-containing composition, in a method to determine the presence and/or concentration of low molecular weight proteins, like Bence Jones proteins, in a test sample by a dry phase, test strip assay procedure.

BACKGROUND OF THE INVENTION AND PRIOR ART

Albumin is the most abundant plasma protein, generally constituting slightly over one-half of the total protein in mammalian plasma. In the human body, albumin has the important role of regulating the water balance between blood and tissues, and of functioning as a transport molecule for various compounds, such as bilirubin, fatty acids, cortisol, thyroxine and drugs such as sulfonamides and barbiturates, that are only slightly soluble in water. An albumin deficiency can restrict the transport of slightly water soluble materials throughout the body and a deficiency is signaled in an individual by an abnormal accumulation of serous fluid, or edema. Therefore, it is clinically important to determine whether an individual has a deficiency of serum albumin.

Likewise, it is clinically important to determine if an individual is excreting an excess amount of protein. A normal functioning kidney forms urine in an essentially two step process. Blood flows through the glomerulus, or glomerular region of the kidney. The capillary walls of the glomerulus are highly permeable to water and low molecular weight components of the blood plasma. Albumin and other high molecular weight proteins cannot pass through these capillary walls and are essentially filtered our of the urine so that the protein is available for use by the body. The liquid containing the low molecular weight components passes into the tubules, or tubular region, of the kidney where reabsorption of some urine components, such as low molecular weight proteins; secretion of other urine components; and concentration of the urine occurs. As a result, through the combined processes of the glomerulus and tubules, the concentration of proteins in urine should be minimal to non-existent. Therefore, abnormally high amounts of albumin and/or low-molecular weight proteins in urine must be detected and related to a physiological dysfunction.

The relatively high concentration of albumin in the urine of an individual usually is indicative of a diseased condition. For example, the average normal concentration of protein in urine varies from about 2 mg/dL to about 8 mg/dL, with approximately one-third of the total urinary protein being serum albumin. However, in a majority of diseased states, urinary protein levels increase appreciably, such that albumin accounts for from about 60 percent to about 90 percent of the excreted protein. The presence of an abnormal increased amount of protein in the urine, known as proteinuria, is one of the most significant indicators of renal disease, and may be indicative of various other non-renal related diseases.

Therefore, in order to determine if an individual has an albumin deficiency and/or to determine if an individual excretes an excess amount of protein, and in order to monitor the course of medical treatment to determine the effectiveness of the treatment, simple, accurate and inexpensive protein detection assays have been developed. Furthermore, of the several different assay methods developed for the detection and/or measurement of protein in urine and serum, the methods based on dye binding techniques have proven especially useful because dye binding methods are readily automated and provide reproducible and accurate results.

In general, dye binding techniques utilize pH indicator dyes that are capable of interacting with a protein, such as albumin, and that are capable of changing color upon interaction with a protein absent any change in pH. When a pH indicator dye interacts with, or binds to, a protein, the apparent pKa (acid dissociation constant) of the indicator dye is altered and the dye undergoes a color transition, producing the so-called "protein-error" phenomenon. In methods utilizing the dye binding technique, an appropriate buffer maintains the pH indicator dye at a constant pH to prevent a color transition of the pH indicator dye due to a substantial shift in pH. Due to the "protein-error" phenomena, upon interaction with the protein, the pH indicator dye undergoes a color transition that is identical to the color change arising because of a change in the pH. Examples of pH indicator dyes used in the dry phase assay of proteins that are capable of interacting with or binding to proteins and exhibiting "protein-error" color transitions include tetrabromophenol blue and tetrachlorophenol-3,4,5,6-tetrabromosulfophthalein.

Although pH indicator dyes have been used extensively in protein assays, several problems and disadvantages still exist in protein assay methods utilizing indicator dyes. For example, methods based upon pH indicator dyes either cannot detect or cannot quantitatively differentiate between protein concentrations below approximately 15 mg/dL. In addition, although several simple semiquantitative tests and several complex quantitative tests are available for the determination of the total protein content in a test sample, the majority of these assay methods, with the notable exception of the simple colorimetric reagent test strip, require the precipitation of protein to make quantitative protein determinations.

The colorimetric reagent test strip utilizes the previously discussed ability of proteins to interact with certain acid-base indicators and to alter the color of the indicator without any change in the pH. For example, when the indicator tetrabromophenol blue is buffered to maintain a constant pH of approximately 3, the indicator imparts a yellow color to solutions that do not contain protein. However, for solutions containing protein, the presence of protein causes the buffered dye to impart either a green color or a blue color to solution, depending upon the concentration of protein in the solution.

Some colorimetric test strips used in protein assays have a single test area consisting of a small square pad of a carrier matrix impregnated with a buffered pH indicator dye, such as tetrabromophenol blue. Other colorimetric test strips are multideterminant reagent strips that include one test area for protein assay as described above, and further include several additional test areas on the same strip to permit the simultaneous assay of other urinary constituents. For both types of colorimetric test strips, the assay for protein in urine is performed simply by dipping the colorimetric test strip into a well mixed, uncentrifuged urine sample, then comparing the resulting color of the test area of the test strip to a standardized color chart provided on the colorimetric test strip bottle.

For test strips utilizing tetrabromophenol blue, buffered at pH 3, as the indicator dye, semiquantitative assays for protein can be performed and are reported as negative, trace, or one "plus" to four "plus". A negative reading, or yellow color, indicates that the urine contains no protein, as demonstrated by the lack of a color transition of the indicator dye. A trace reading may indicate from about 5 to about 20 mg/dL of protein in the urine. The one "plus" to four "plus" readings, signified by color transitions of green through increasingly dark shades of blue, are approximately equivalent to urine protein concentrations of 30, 100, 300, and over 2000 mg/dL, respectively, and serve as reliable indicators of increasingly severe proteinuria.

In accordance with the above-described method, an individual can readily determine, visually, that the protein content of a urine sample is in the range of 0 mg/dL to about 30 mg/dL. However, the color differentiation afforded by the presently available commercial test strips is insufficient to allow an accurate determination of protein content in urine between 0 mg/dL and about 15 mg/dL. The inability to detect and differentiate between low protein concentrations is important clinically because a healthy person usually has a urine protein level in the range of about 10 mg/dL to about 20 mg/dL. Therefore, it could be clinically important to know more precisely the urine protein content of an individual, rather than merely estimating the protein content at some value less than about 30 mg/dL.

Of course, the protein content of a urine sample can be determined more precisely by semiquantitative protein precipitation techniques or by quantitative 24 hour protein precipitation techniques. However, these tests are time consuming and relatively expensive. Furthermore, the precipitation tests must be run in a laboratory by trained personnel, and therefore are unavailable for the patient to perform at home to quickly determine urine protein content and to monitor the success or failure of a particular medical treatment.

Therefore, it would be extremely advantageous to have a simple, accurate and trustworthy method of assaying urine for protein content that allows visual differentiation of protein levels in the ranges of 0 mg/dL to about 10 mg/dL, about 10 mg/dL to about 20 mg/dL, and about 20 mg/dL to about 30 mg/dL, and upwards to between about 100 mg/dL to about 300 mg/dL. By providing such an accurate method of determining urine protein concentration in an easy to use form, such as a dip-and-read test strip, the urine assay can be performed by laboratory personnel to afford immediate test results, such that a diagnosis can be made without having to wait up to one day for assay results and medical treatment can be commenced immediately. In addition, the test strip method can be performed by the patient at home to more precisely monitor low levels of protein in urine and/or the success of the medical treatment the patient is undergoing.

As will be described more fully hereinafter, the method of the present invention allows the fast, accurate and trustworthy protein assay of urine by utilizing a test strip that includes a dual indicator reagent composition. The dual indicator reagent composition improves the visual color resolution, and therefore the sensitivity, of the assay, thereby allowing urine protein concentrations to be accurately determined at levels of approximately 30 mg/dL or less. In addition, the method of the present invention can be used to determine the presence and/or concentration of low molecular weight proteins, such as Bence Jones proteins, in a test sample. All prior art assay techniques for low molecular weight proteins involve immunoelectrophoresis methods or heat test methods that are time consuming, relatively expensive and are not amenable for use by the patient at home to detect low molecular weight proteins in urine.

Bence Jones proteins belong to a class of urinary proteins having a low molecular weight of approximately 20,000 and that are small enough to pass through the glomerular filters of the kidney. However, the Bence Jones proteins usually are reabsorbed in the tubular section of the kidney. Therefore, the concentration of Bence Jones proteins is negligible in the urine of a healthy person. As a result, a significant amount of Bence Jones proteins in urine generally is clinically significant. Overall, the detection and measurement of the concentration of low molecular weight proteins in urine is important because certain diseases are characterized by the excretion of specific low molecular weight proteins (globulins) rather than by diffuse proteinuria characterized by elevated albumin levels.

For example, the Bence Jones proteins represent a portion of the high molecular weight plasma myeloma globulin, and therefore are found in increased amounts in the urine of more than one-half of the patients suffering from multiple myeloma or leukemia. Bence Jones proteinuria also is found in the urine of many patients suffering from macroglobulinemia and primary systemic amyloidosis. In addition, an increased excretion of a specific globulin that is similar to Bence Jones proteins occurs in Franklin's disease; and patients with renal tubular disorders, such as the Fanconi syndrome, show a substantial increase in the quantity of globulins excreted in the urine. Accordingly, investigators have searched for a simple assay for low molecular weight proteins because the dye-binding method used in commercially available test strips is insensitive to low molecular weight proteins, like Bence Jones proteins. Surprisingly and unexpectedly, the method of the present invention provides a technique to detect and measure the concentration of low molecular weight proteins, like Bence Jones proteins using a dual indicator reagent composition incorporated into a polymerized urethane-containing film, layer or membrane having an appropriate pore size.

The Bence Jones proteins differ from all other urinary proteins in that they coagulate upon heating to temperatures between about 45° C. and about 60° C., and then redissolve on further heating to the boiling point of test sample. This peculiar characteristic of Bence Jones proteins has been the basis of all qualitative and semiquantitative determinations for Bence Jones proteins. The dye binding technique used in commercially available test strips has proved insensitive to Bence Jones proteins because the much greater relative concentration of higher molecular weight proteins, such as albumin, in the urine of a healthy individual effectively interferes with and masks the presence of Bence Jones proteins. Furthermore, it is inconvenient and costly to separate the albumin from Bence Jones proteins, thereby negating the utility of separating the albumin from the Bence Jones proteins before using a dry phase test strip.

As a result, dry phase test strips are presently unavailable to test for the presence and concentration of Bence Jones proteins in urine. However, incorporating the highly sensitive dual indicator reagent composition of the present invention into a carrier matrix having a sufficiently small pore size prevents the albumin content of the urine sample from penetrating the carrier matrix and interacting with the dual indicator reagent composition to cause a color transition. However, the carrier matrix is of sufficient pore size to allow Bence Jones proteins to penetrate the carrier matrix and to interact with the dual indicator reagent composition to cause a color transition.

Proteinuria resulting either from abnormally high albumin levels or the presence of low-molecular weight proteins depends upon the precise nature of the clinical and pathological disorder and upon the severity of the specific disease. Proteinuria can be intermittent or continuous, with transient, intermittent proteinuria usually being caused by physiologic or functional conditions rather than by renal disorders. Therefore, accurate and thorough assays of urine and other test samples for protein must be available for both laboratory and home use. The assays must permit the detection and measurement of the proteins of interest, either albumin and/or Bence Jones proteins, such that a correct diagnosis can be made and correct medical treatment implemented, monitored and maintained. In addition, it would be advantageous if the protein assay method, both for high molecular weight proteins, like albumin, and low molecular weight proteins, like Bence Jones proteins, could be utilized in a dip-and-read format for the easy and economical, qualitative and/or semiquantitative determination of protein in urine or other test samples.

Furthermore, any method of assaying for protein in urine or other test samples must yield accurate, trustworthy and reproducible results by utilizing a composition that undergoes a color transition as a result of an interaction with protein, and not as a result of a competing chemical or physical interaction, such as a pH change or preferential interaction with a test sample component other than protein. Moreover, it would be advantageous if the protein assay method is suitable for use both in wet assays and in dry reagent strips for the rapid, economical and accurate determination of protein in urine or other test samples. Additionally, the method and composition utilized in the assay for protein should not adversely affect or interfere with the other test reagent pads that are present on multiple test pad strips.

Prior to the present invention, no known method of assaying urine or other test samples for proteins included a dual indicator reagent composition that improves color resolution of the assay and increases the sensitivity of the assay at lower protein concentration levels, such that accurate and trustworthy protein assays can be made for protein concentrations of about 30 mg/dL and below. In addition, although a dry phase chemistry test strip utilizing a single dye, such as tetrabromophenol blue or tetrachlorophenol-3,4,5,6-tetrabromosulfonephthalein, has been used extensively for several years, no dry phase test strip has incorporated two dyes to improve visual color resolution, and therefore increase sensitivity, at lower protein concentration levels. Furthermore, until the method of the present invention, dry phase test strip procedures were available principally to test for total protein concentration, i.e., for albumin. However, surprisingly and unexpectedly, the method of the present invention permits the dry phase test strip assay of urine and other test samples for low molecular weight proteins, such as Bence Jones proteins.

The prior art contains numerous references on the wet phase and the dry phase chemistry utilized in the pH indicator dye method of assaying urine for proteins. For example, Keston U.S. Pat. No. 3,485,587 discloses the basic dye binding technique used to assay for proteins at a constant pH. Keston teaches utilizing a single indicator dye, maintained at a constant pH slightly below the pKa (acid dissociation constant) of the dye, to determine the presence and/or concentration of albumin by monitoring the color transition of the dye.

In contrast to the prior art, and in contrast to the presently available commercial test strips, the method of the present invention provides increased sensitivity in the detection and measurement of proteins in urine by utilizing a combination of indicator dyes, such that accurate protein levels of about 30 mg/dL and below can be determined. Unexpectedly and surprisingly, the method of the present invention also allows the simple and essentially immediate detection and measurement of low levels of Bence Jones proteins; a method heretofore impossible because of interference by the relatively high concentration of albumin in the urine sample. Hence, in accordance with the method of the present invention, new and unexpected results are achieved in the dry phase reagent strip assay, and the wet assay, of urine and other test samples for proteins, including low molecular weight proteins, by utilizing a dual indicator reagent composition incorporated into a carrier matrix having an appropriate pore size.

SUMMARY OF THE INVENTION

In brief, the present invention is directed to a new and improved test device, method of manufacturing the test device, and method of determining the presence and/or concentration of a component in a test sample. The device includes a carrier matrix incorporating a reactant composition capable of interacting with a test sample component to produce a detectable response. For home use, the reactant composition produces a visually detectable response. For laboratory use, the reactant composition produces a response that is detectable visually or by instrument. The carrier matrix of the device of the present invention comprises such bibulous porous materials as filter paper, or a new and improved nonbibulous protein permeable strip, layer or membrane of a polymerizable urethane-containing material. A reactant composition can be homogeneously incorporated into the polymerizable carrier matrix prior to or after complete curing of the matrix, and the carrier matrix then holds the reactant composition homogeneously throughout the carrier matrix in a known concentration while maintaining carrier matrix penetrability of the predetermined component after complete curing of the carrier matrix.

More particularly, the present invention is directed to a method of assaying urine or other test samples for proteins by utilizing a new and improved dual indicator reagent composition. It has been demonstrated that employing a combination of indicator dyes, capable of undergoing color transitions in approximately the same pH range, affords improved color resolution and increased sensitivity at low protein concentration ranges. In accordance with an important feature of the present invention, the qualitative and/or semiquantitative determination of protein levels between 0 mg/dL and about 2000 mg/dL, and especially between 0 mg/dL and about 30 mg/dL, in urine and other test samples is accomplished. By utilizing the dual indicator reagent composition of the present invention in clinical test methods, the qualitative and/or semiquantitative concentration of proteins, such as albumin, in urine or other test sample can be more accurately determined because improved color resolution afforded by the combination of dyes increases the sensitivity of the method to low concentrations of protein. Furthermore, surprisingly and unexpectedly, the dual indicator reagent composition incorporated into a test device including a new and improved polyurethane-based carrier matrix allows the detection and measurement of low molecular weight proteins, such as Bence Jones proteins, in urine and other test samples.

Therefore, it is an object of the present invention to provide a new and improved method and test device for determining the relative concentration of a chemical compound in a liquid.

Another object of the present invention is to provide a simple, trustworthy, accurate and reproducible method of assaying urine or other test samples for proteins.

Another object of the present invention is to provide a new and improved protein interactive test device for interaction with protein in a test fluid to produce a visible change, such as a change in color, of the test device, indicative of the protein concentration in the test fluid.

Another object of the present invention to provide a method of assaying urine or other liquid test samples for albumin or low molecular weight proteins, such as Bence Jones proteins.

Another object of the present invention is to provide a method of assaying urine or other liquid test samples that provides improved visual color resolution and increased sensitivity to low protein concentrations.

Yet another object of the present invention is to provide a method of assaying urine or other liquid test samples that is sensitive to protein concentrations of less than about 15 mg/dL and that semiquantitatively discriminates between protein levels of from 0 mg/dL to about 2000 mg/dL, and especially from 0 mg/dL to about 30 mg/dL.

Another object of the present invention is to provide a method of assaying urine or other test liquids that utilizes a dual indicator reagent composition.

Another object of the present invention is to provide a method of assaying urine or other test liquids by utilizing a dual indicator reagent composition that, when buffered in the pH range slightly below the color transition pH of the indicator components of the composition, can interact with proteins and undergo a detectable and measurable color transition to establish the presence and concentration of protein in the test sample.

Another object of the present invention is to provide a dual indicator reagent composition that, when appropriately buffered, can interact with proteins and undergo a visually and/or instrumentally differentiable color transition to allow the semiquantitative determination of the concentration of protein in the urine or other liquid samples at levels between 0 mg/dL and about 2000 mg/dL, and especially between 0 mg/dL and about 30 mg/dL.

Another object of the present invention is to provide a method of assaying urine or other test samples for the presence and concentration of low molecular weight proteins.

Still another object of the present invention is to provide a method of assaying a liquid sample for low molecular weight proteins, including Bence Jones proteins, by utilizing a dual indicator reagent composition.

Another object of the present invention is to provide a method of assaying for Bence Jones proteins by incorporating the dual indicator reagent composition into a dry phase detection device, comprising a carrier matrix having a porosity sufficient to allow penetration by low molecular weight proteins, such as Bence Jones proteins, but to preclude penetration by higher molecular weight proteins, such as albumin.

Another object of the present invention is to provide a method of manufacturing a detection device for low molecular weight proteins comprising a dual indicator reagent composition incorporated into a carrier matrix of suitable porosity.

Another object of the present invention is to provide a new and improved test device and method of manufacturing the test device including a carrier matrix having incorporated therein during manufacture thereof, a reactant composition capable of interacting with a chemical compound in a test sample, wherein the carrier matrix comprises a polymerizable urethane-containing composition.

Another object of the present invention is to provide a reagent strip comprising a carrier matrix comprising a polymerizable urethane-containing composition capable of relatively homogeneous mixture with a dual indicator reactant composition prior to curing and permeable to low molecular weight proteins after curing.

Another object of the present invention is to provide a new and improved test device and method of manufacturing the test device for sensing the presence of a chemical compound in a liquid, where the chemical compound is capable of permeating a polymer-based carrier matrix and capable of reacting with a dual indicator reagent composition incorporated into the carrier matrix during manufacture prior to complete curing of the carrier matrix or after complete curing of the carrier matrix.

A still further object of the present invention is to provide a new and improved dry phase test strip capable of incorporating a dual indicator reactant composition into the carrier matrix during or after manufacture to achieve a test strip of new and unexpected precision in protein response.

Another object of the present invention is to provide a new and improved reagent test strip, capable of interacting with a predetermined protein component in an assay medium, having a dual indicator reactant composition incorporated into a carrier matrix comprising a cured polymer layer, film or membrane permeable to the predetermined protein component of the assay medium.

Another object of the present invention is to provide a new and improved test device for the quantitative analysis of proteins, including low molecular weight proteins.

BRIEF DESCRIPTION OF THE DRAWINGS

The above and other objects and advantages and novel features of the present invention will become apparent from the following detailed description of the preferred embodiments of the invention illustrated in the accompanying figures illustrating the enhanced color resolution of the color transition in the reagent test strips and the increased sensitivity to proteins, permitting more accurate semiquantitative analyte determinations.

DETAILED DESCRIPTION OF THE INVENTION

Figure 1:
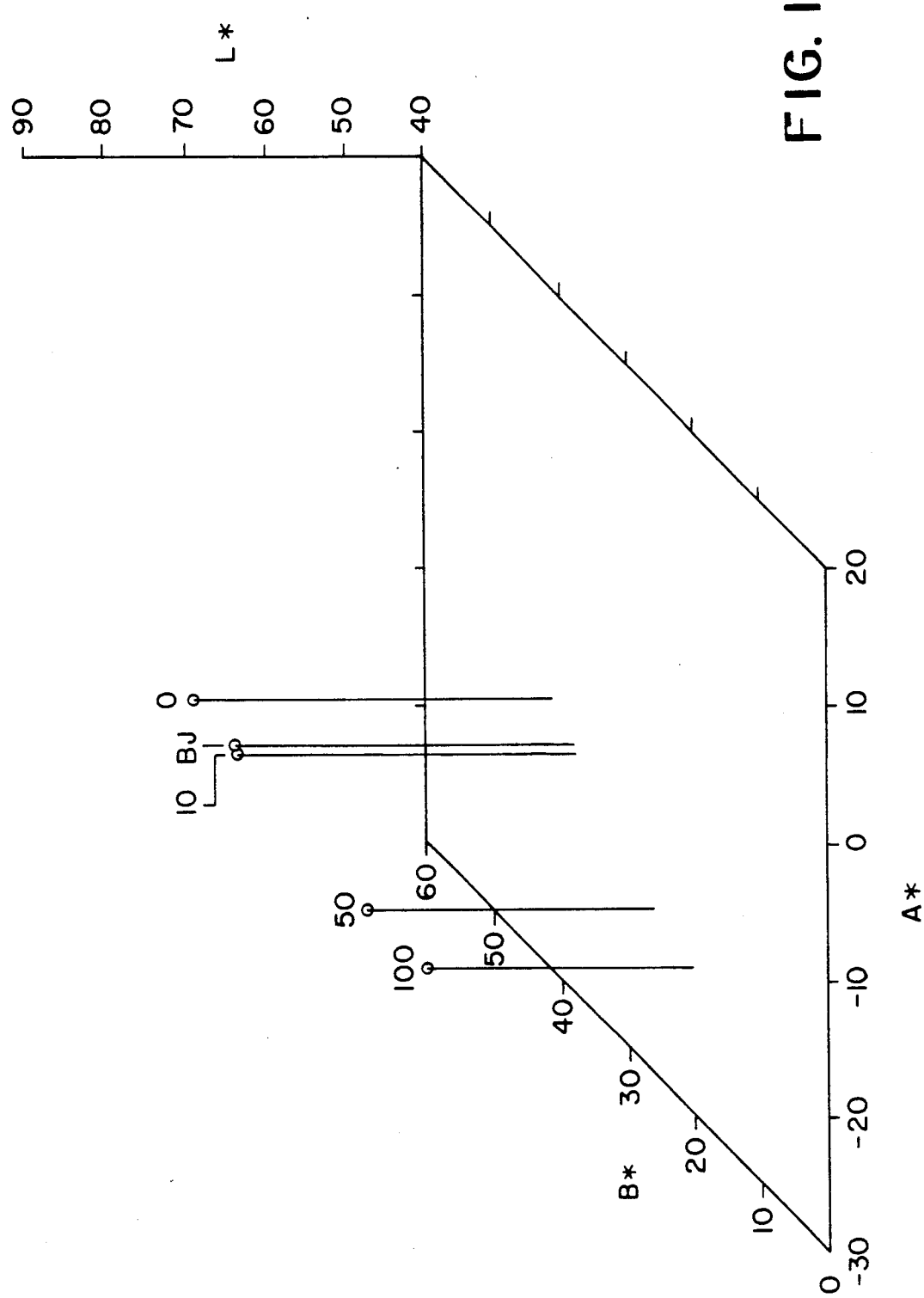
FIG. 1 is a color space plot showing the assay of liquid samples containing 0, 10, 50 and 100 mg/dL of albumin respectively and 100 mg/dL of Bence Jones proteins using a dry phase test strip comprising a filter paper bibulous matrix incorporating the single indicator dye tetrabromophenol blue (TBPB)

In accordance with the method of the present invention, the qualitative and/or semi-quantitative assay for proteins, including albumin and/or low molecular weight proteins, in urine and other test samples is accomplished by utilizing a dual indicator reagent composition. By employing a combination of suitable indicator dyes, visual color resolution is improved over assays employing a single indicator dye, and the sensitivity of the assay to low concentration levels of protein is increased. The improved color resolution and increased sensitivity to low protein levels afforded by the method of the present invention is especially useful in urine assays.

Present-day commercial assays are incapable of differentiating between protein levels ranging from 0 mg/dL to about 30 mg/dL, and especially from 0 mg/dL to about 15 mg/dL. Differentiating between low protein concentration levels is clinically important in the art because a range of from about 10 mg/dL to about 20 mg/dL is used as the normal urine protein level for a healthy individual, therefore urine protein levels from 0 mg/dL to about 10 mg/dL may indicate a potential protein deficiency that can cause physiological imbalances and urine protein levels greater than about 20 mg/dL may indicate an excessive excretion of proteins that can signify a diseased state. It should be noted that in regard to urine protein concentrations in the relatively high range, such as from about 100 mg/dL to about 2000 mg/dL, the method of the present invention still affords improved color resolution and increased sensitivity to urine protein concentration, however such clinical benefits are less critical in this concentration range since such high protein levels are definitely indicative of an abnormal physiological state that must be investigated further.

In further regard to urine assays, the presence of low levels of low molecular weight proteins, such as Bence Jones proteins, is indicative of specific diseased states, such as leukemia or multiple myeloma. Therefore, in accordance with another important feature of the device and method of the present invention, the improved color resolution afforded by the use of the dual indicator reagent composition and the resulting increased sensitivity to low levels of protein in urine provides a technique to detect and measure the concentration of low molecular weight proteins present in urine. Therefore, as will be discussed more fully hereinafter in the detailed description of the invention, a method and device is available to test either for total urine protein content in urine, or for the low molecular weight protein content in urine by eliminating the interferences caused by the higher molecular weight proteins, such as albumin.

Furthermore, it will become apparent that in addition to assaying urine, the method and device of the present invention also can be used to determine the presence and semiquantitive concentration of albumin in blood plasma and serums; and more generally, the albumin content of many other albumin-containing fluids as well. In accordance with another important feature of the present invention, the method and composition of the present invention can be employed both in aqueous, liquid phase assays and, to achieve the full advantage of the present invention, in dry phase, test pad assays to determine the presence and/or concentration of proteins in urine or other liquid test samples.

Surprisingly and unexpectedly, it has been found that combining two suitable indicator dyes, each having the ability to interact with proteins and undergo a detectable and measurable color transition while maintained at a constant pH, demonstrated improved color resolution and increased sensitivity to low protein concentrations when used in a dye-binding technique to determine the presence and/or concentration of proteins in a test sample. The dye-binding technique using the dual indicator reagent composition provides a more accurate, trustworthy and clinically significant semiquantitative assay for protein. Presently, both liquid phase assays and commercially available dry phase, test strip assays utilize only a single dye, such as tetrabromophenol blue or tetrachlorophenol-3,4,5,6-tetrabromosulfonephthalein, as the indicator dye to determine the presence and/or semiquantitative concentration of protein in a test sample.

The dyes presently used in assays for protein interact with proteins and undergo a color transition due to the protein-error phenomena when maintained at the proper, constant pH. The protein-error phenomena is fully described in Keston U.S. Pat. No. 3,485,587, wherein the various dyes, the correct pH ranges and the buffers required to observe the protein-error phenomena are disclosed. The Keston patent basically describes the present day dry phase test strips employed to assay for total protein content in urine. These total protein test strips generally include an indicator dye that normally undergoes a color transition at a strongly acidic pH of 5 or below, and a buffer to maintain the pH of the indicator dye slightly below the pH of color transition for the dye. A sufficient buffering of the indicator dye essentially assures that the dye changes color due to an interaction with protein rather than due to a pH change occurring upon contact with the test sample.

In accordance with an important feature of the present invention, it has been demonstrated that a judicious selection of a pair of indicator dyes, properly buffered at a suitable pH, provides a more accurate and trustworthy assay for total protein content in liquid samples. Furthermore, both surprisingly and unexpectedly, by incorporating a dual indicator reagent composition in a dry phase test stick comprising a carrier matrix comprising a polymerized urethane-containing film, layer or membrane, the selective detection and measurement of low molecular weight proteins in a test sample is accomplished. In addition, the detection and measurement of the low molecular weight protein is achieved without having to separate the predominant, competing and interfering higher molecular weight proteins, such as albumin, from the test sample. Therefore, a time-consuming and expensive additional manipulative step is avoided. Furthermore, a method of fast, accurate, reproducible and trustworthy assays, performable at home or in the laboratory to yield essentially immediate assay results for low molecular weight proteins, is achieved.

In order to achieve the benefits afforded by the present invention, it is imperative that the dual indicator reagent composition includes a suitable combination of indicator dyes. In contrast both to the prior art and to presently available commercial assays that utilize a single indicator dye, the incorporation of two indicator dyes, each having an essentially identical color transition pH range and neither undergoing an identical color transition, improves the color resolution and differentiation, both visually and instrumentally, of the color transition occurring upon interaction with proteins. Therefore, the sensitivity of the protein assay, especially at relatively low protein concentrations, is increased.

The method of the present invention utilizes the "protein-error" phenomena previously discussed. However, the incorporation of two indicator dyes into the dual indicator reagent composition introduces the principle of competitive interaction between each of the two indicator dyes for the available protein in the test sample at a controlled pH. As previously described, when a pH indicator dye interacts with a protein, the apparent pKa of the dye is altered and a color transition occurs producing the so-called "protein-error" phenomenon. However, by employing two indicator dyes, each having an approximately identical color transition pH range, two color transitions are observed simultaneously. By adjusting the relative amounts of the two indicator dyes, in relation to the ability of each dye to interact with protein and in relation to the actual color transition and the intensity of color transition of each dye, a more spectacular color development is achieved, therefore improving color resolution and differentiation upon interaction with proteins and accordingly increasing assay sensitivity.

In general, any two pH indicator dyes can be utilized in the method of the present invention, provided that three basic requirements are satisfied. Initially, it is of primary importance that each dye is capable of interacting with proteins and undergoing a detectable and measurable color transition in response to the protein interaction. The indicator dyes utilized in the dual indicator reagent composition must preferentially interact with proteins as opposed to any competing chemical or physical interactions with non-protein components in the test sample. Any appreciable competing interactions with non-protein components could lead to false and erroneous assays concerning the presence and amount of protein in the test sample. For example, the proper buffering of the indicator dyes precludes the possibility of a color transition occurring because of a pH change in all cases except those wherein the test sample is sufficiently alkaline to overcome the effect of the buffers.

In addition, it is important that each dye has a relatively similar affinity to interact with proteins. It has been found that if one dye has more than an approximately ten to approximately fifteen times greater affinity to proteins than the second dye, erroneous and false assays may result because preferential interaction of one dye with the protein produces a color transition that does not accurately correlate to the concentration of protein in the sample. The inability of the second dye to effectively interact with the proteins can lead to erroneously high or erroneously low results because only the first dye will undergo a color transition in response to the protein interaction, and this color transition will not be balanced and modified by a second color transition occurring in response to the interaction of the second dye with the proteins present in the test sample.

Secondly, each of the indicator dyes utilized in the dual indicator reagent composition must undergo a color transition at approximately the same pH range. Normally, a difference in pH range for color transition between the two dyes of up to about 0.5 pH units is acceptable; however, to achieve the full advantage of the present invention, the difference in pH range for color transition between the two dyes is preferably limited to about 0.2 to about 0.3 pH units. An equal or approximately equal, pH color transition range is required because in the dye binding technique the indicator dye is maintained at a constant pH, usually slightly below the color transition pH range of the dye, to assure that the color transition occurs because of an interaction with a protein and not because of a pH change. In accordance with the method of the present invention, each dye is buffered to a pH value slightly below the pH range wherein the dye changes color, in order for each dye to undergo its maximum color transition, and therefore most appreciably improve color resolution and most substantially increase assay sensitivity. Therefore, to maximize the color transition for the dual indicator reagent composition as a whole, the two indicator dyes must undergo a color transition at approximately the same pH range.

Finally, the dyes employed in the dual indicator reagent composition must undergo color transitions that do not mutually interfere with one another. For example, the benefits of improved color resolution and increased assay sensitivity can be defeated or minimized if each dye undergoes a color transition from a less intense color to a more intense color. Similarly, the benefits afforded by the present invention also are minimized or negated in situations wherein the first dye undergoes a color transition to match the original color of the second dye, and the second dye undergoes a color transition to match the original color of the first dye. For example, if at a constant pH, and prior to interaction with a protein, the first dye is red in color and the second dye is colorless; then upon interaction with protein in a test sample, the first dye undergoes a color transition from red to colorless and the second dye undergoes a color transition from colorless to red, the benefits of improved color resolution and assay sensitivity are diminished or negated, regardless of whether the assay is monitored visually or by instrument. Therefore, in order to achieve the full advantage of the present invention, the dyes employed in the dual indicator reagent composition are selected such that one dye changes from a more intense color to a less intense color, and the second dye changes from a less intense color, that differs from the less intense color of the first dye, to a more intense color that differs from the more intense color of the first dye.

It has been found that any pH indicator dye can be used in the method of the present invention, provided that both dyes of the dual indicator reagent composition are capable of interacting with proteins to undergo a sufficient and contrasting color transition at approximately the same pH range. Depending upon several chemical and physical parameters, such as ability to interact with proteins, intensity of the color transition and chemical compatibility between the dyes, the ratio of the first indicator dye in the dual indicator reagent composition to the second indicator dye of the reagent composition can range from approximately 5 to 1 to approximately 1 to 5, and preferentially from about 3 to 1 to about 1 to 3. The exact ratio of the first indicator dye to the second indicator dye of the dual indicator reagent composition can be determined by those skilled in the art of designing test kits in order to produce an assay for proteins having maximum visual color resolution and maximum sensitivity. The indicator dyes utilized in the dual indicator reagent composition of the present invention can be prepared by methods well known to persons in the art. Furthermore, several indicator dyes that are useful in the method of the present invention are well known acid-base indicator dyes that are presently available commercially.

A combination of indicator dyes as described above is utilized as an indicator reagent composition in an improved method to determine the presence and/or the semiquantitative concentration of protein in urine or other liquid test samples. It has been demonstrated that the dual indicator reagent composition of the present invention interacts with proteins to produce a differentiable and measurable color transition, either visually and/or by instrument, due to the "protein-error" phenomena. However, in addition to the combination of dyes, the dual indicator reagent composition of the present invention may require a sufficient amount of a proper buffer, such that the dyes will not change color as a result of a pH shift, but will change color upon contact and interaction with proteins to accurately establish the presence and/or semiquantitative concentration of protein in the test sample.

Further, it has been demonstrated that any of various known types of buffers can be used in the dual indicator reagent composition of the present invention. The function of the buffer is to maintain the reagent composition at a substantially constant pH to produce the desired color transition in the indicators because of the presence of proteins and to essentially eliminate color changes due to a variation in the pH of the protein-containing test sample. As a result, the amount of buffer incorporated into the dual indicator reagent composition depends upon the nature of the test sample. The quantity of buffer usually falls between about 100 millimolar (mM) and about 500 millimolar, although in particular cases the amount of buffer can be above or below this range. The nature of the buffer used will depend upon, and vary with, the indicators incorporated into the dual indicator reagent composition. However, it has been found that for optimum results, the pH of the reagent composition generally should be maintained at a pH value only slightly below the pH range wherein the two indicator dyes of the reagent composition undergo a color transition. A method of determining a suitable buffered pH value for the particular indicator dyes of the reagent composition and of determining the particular buffer than can be used in the dual indicator reagent composition is found in Keston, U.S. Pat. No. 3,485,587.

Although the use of a buffer in the present dual indicator reagent composition is preferred, a buffer is not essential in all cases. For example, in special cases it may be desirable to add a buffer to the urine or other test sample before the test sample contacts the dual indicator reagent composition. Also the test sample may already contain a buffer of the proper type and in the proper amount to maintain the composition at a constant pH, or the dual indicator dye composition may be insensitive to pH changes. In such cases, the two indicator dyes can be the sole active ingredients in the dual indicator reagent composition. However, it should be understood that optional ingredients, such as surfactants, that do not materially alter the nature and the function of the indicator dyes and/or the buffer and that do not interfere with the protein assay, also can be included in the dual indicator reagent composition. Likewise, other such non-essential ingredients include nonactive background dyes, polymers and plasticizers.

Upon contact with the urine or other test sample, a color transition of the dual indicator reagent composition demonstrates the presence of protein. Furthermore, the intensity and degree of the color transition can be used to determine the semiquantitative concentration of protein in the test sample by comparing or correlating the color produced by the test sample to colors produced by solutions having a known concentration of protein. In accordance with an important feature of the present invention, it has been demonstrated that the dual indicator reagent composition provides a sufficiently resolved and differentiated color transition such that the amount of protein in the test sample can be measured and accurately determined without the use of color-measuring instruments, such as spectrophotometers or colorimeters. However, if desired, such color-measuring instruments can be used to measure the difference in color degree and intensity between the test sample and a solution of known albumin concentration.

Accordingly, an assay for protein that utilizes a suitably buffered dual indicator reagent composition improves the accuracy and reliability of the assay and also increases physician confidence in the assay. Additionally, because of the number of urine assays for protein being performed at home by the untrained patient, as opposed to trained physicians or technicians in the laboratory, it is imperative to provide accurate and reliable semiquantitative assay methods for protein content in the urine.

In accordance with an important feature of the present invention, TABLE I tabulates representative pH indicator dyes that can be used as protein indicator dyes in the dual indicator reagent composition of the present invention. TABLE I includes indicator dyes that are presently used in assays for protein, plus several other suitable indicator dyes that undergo a color transition in the pH range of approximately 2.8 to approximately 5.2

TABLE I

PROTEIN INDICATOR DYES

| Indicator Dye | Color Transition | Approximate pH of Color Transition |
|---|---|---|
| Bromochlorophenol Blue (BCPB) | Yellow-Green | 2.8 |
| Iodophenol Blue (IPB) | Yellow-Blue | 2.8 |
| Rose Bengal (RB) | Colorless-Pink | 2.8 |
| Bromophenol Blue (BPB) | Yellow-Blue | 3.0 |
| Methyl Orange (MO) | Red-Yellow | 3.0 |
| Tetrabromophenol Blue (TBPB) | Yellow-Blue | 3.3 |
| Bromopyrogallol Red (BPGR) | Yellow-Red | 3.5 |
| Bromocresol Green (BCG) | Yellow-Green | 4.3 |
| Tetrabromophenol-phthalein ethyl ester (TBEE) | Yellow-Green | 4.3 |
| Bromophenol Red (BPR) | Yellow-Red | 4.7 |
| HLO 301* | Colorless-Green | 4.7 |
| Bromocresol Purple (BCP) | Yellow-Purple | 5.2 |

*HLO 301 is a tetracyclic dye having the chemical name 8-amino-11-aza-6-thia-[5,12-naphthacene-quinone].

The list of protein indicator dyes in TABLE I is a partial list including dyes that undergo a color transition at an acidic pH. In general, assays for protein have been conducted at an acidic pH and using an indicator dye undergoing a color transition at an acidic pH because the indicator dye can interact more strongly with the protein at low, acidic pH values. The increased interaction between the indicator dye and the protein at low pH values occurs because of a strong attraction between the positively-charged cationic protein molecule and the negatively-charged anionic indicator dye molecule, and, additionally, because the acidic conditions serve to partially denature proteins and therefore increase the ability of the protein to interact with the indicator dye. However, it should be understood that other indicator dyes, capable of interacting with proteins and undergoing a color transition at a pH value above approximately 5.2, also can be employed in the method of the present invention.

Accordingly, other indicator dyes, capable of undergoing a color transition either in the acidic or in the neutral to alkaline pH range, also can be combined to yield a dual indicator reagent composition to afford improved color resolution and differentiation and increased assay sensitivity. However, each indicator dye included in the dual indicator reagent composition must be capable of interacting with proteins, the two dyes must undergo color transitions within approximately the same pH range and the dyes must undergo sufficiently different color transitions. Examples of other pH indicator dyes that can be used in the method of the present invention, and having a pH of color transition ranging from as low as 0.15 to as high as 14 are found in *The Merck Index, Ninth Edition*, pages MISC-94 and MISC-95 (1976) and in *Handbook of Chemistry and Physics*, 51st Edition, pages D-106 through D-109 (1970-1971). In addition, several other suitable pH indicator dyes are available commercially from numerous manufacturers and distributors.

In accordance with an important feature of the present invention, several suitable combinations of indicators are envisioned from the indicators listed in TABLE I. For example, methyl orange (MO) can be combined with bromochlorophenol blue (BCPB), bromophenol blue (BPB), tetrabromophenol blue (TBPB), or iodophenol blue (IPB) to produce a color transition that provides enhanced color resolution, and therefore increased assay sensitivity. In each case, the intense red color of methyl orange (MO) will predominate prior to interaction with a protein; whereas after protein interaction and dye color transition, the resulting yellow color of methyl orange (MO) will be overcome by the more intense green or blue of the second dye. In addition, each of these second indicator dyes (BCPB, BPB, TBPB and IPB) and methyl orange (MO) is capable of interacting with proteins, and each second indicator dye has an approximate pH of color transition equal to, or approximately equal to, the pH of color transition for methyl orange (MO). Accordingly, it should be noted that rose bengal (RB) may not be suitable indicator dye to be combined with methyl orange (MO) to yield a dual indicator reagent composition. Although rose bengal (RB) can interact with proteins and has a pH of color transition that approximates the pH of color transition for methyl orange (MO), the color transition of rose bengal (RB) from colorless to pink is sufficiently similar to the color transition of methyl orange from red to yellow such that the benefits of increased color resolution, and therefore improved assay sensitivity, may not be achieved.

In another example, bromophenol red (BPR), having a yellow to red color transition, can be combined with bromocresol green (BCG), having a yellow to green color transition, to give a color spectrum of yellow to green to purple, in response to an increasing protein content of the test sample. Similarly, bromophenol red (BPR), having a color transition of yellow to red, can be combined with 8-amino-11-aza-6-thia-[5,12-naphthacenequinone] (HLO 301), having a color transition of colorless to green, to give a color spectrum of yellow to orange to violet, in response to an increasing protein content of the test sample.

To demonstrate the new and unexpected results achieved by the method of the present invention, a dual indicator reagent composition, including the indicators bromophenol blue (BPB) and methyl orange (MO), was prepared, then used in an aqueous, liquid phase assay for total protein content of a test sample. Both bromophenol blue (BPB) and methyl orange (MO) interact with proteins and undergo a color transition at approximately the identical pH of 3. The bromophenol blue (BPB) changes color from yellow to a deep blue and the methyl orange (MO) changes color from a deep red to yellow. A dual indicator reagent composition including the appropriate amounts of bromophenol blue (BPB) and methyl orange (MO), along with a suitable buffer produced the color transitions summarized in TABLE II upon contact with standardized protein solutions.

TABLE II

COLOR TRANSITION OF METHYL ORANGE-BROMOPHENOL BLUE DUAL INDICATOR REAGENT COMPOSITION UPON INTERACTION WITH STANDARDIZED PROTEIN SOLUTIONS (pH = 3.2)

| Concentration of Standardized Protein Solution (mg/dL) | Observed Color |
| --- | --- |
| 0 (blank) | red or orange |
| 10 (trace) | yellow or very light green |
| 20 | light green |
| 30 | green |
| 60 | blue green |
| 100 | blue |
| 300 | dark blue |

In accordance with an important feature of the present invention, the improved color resolution achieved by using the methyl orange-bromophenol blue dual indicator reagent composition permits detection and differentiation between protein concentrations of 0, 10, 20 and 30 mg/dL. In contrast, all prior art methods employing a single indicator dye are unable to differentiate between protein levels in the 0 to about 15 mg/dL range and provide only minimal differentiation between protein levels ranging from 0 to about 30 mg/dL. However, in accordance with the present invention, increased assay sensitivity is achieved, especially at test sample protein levels of about 30 mg/dL and below to ultimately yield more accurate and meaningful assay results.

To perform an aqueous, liquid phase assay for total protein content, the dual indicator reagent composition is produced first. For example, a dual indicator reagent composition is produced by dissolving 0.60g (0.90 millimole) of bromophenol blue (BPB) and 0.60g (1.83 millimole) of methyl orange (MO) in a sufficient amount of a 100 mM citrate buffer to yield one liter of an aqueous dual indicator reagent composition that is 0.9 mM in bromophenol blue (BPB) and 1.83 mM in methyl orange (MO) buffered at pH 3.2. The presence and concentration of protein in a urine sample then was determined by adding one drop (approximately 50uL (microliters)) of urine to one mL of the dual indicator reagent composition The color of the resulting aqueous solution changed from red to blue, therefore revealing the presence of approximately 100 mg/dL of protein in the urine sample.

In general, in the aqueous, liquid phase assay for protein, the dual indicator reagent composition is present in a sufficient amount to allow the visual and/or instrumental detection and measurement of a color transition. However, an excess amount of dual indicator reagent composition should be avoided such that any non-specific interactions with non-protein test sample components are essentially precluded. Usually, a total concentration of dyes in the dual indicator reagent composition in the range of about 0.5 mM to about 5 mM is sufficient to provide a detectable and differentiable color transition, either visually and/or by instrument, and to eliminate or minimize assay interference through dye interaction with non-protein test sample components. To achieve the full advantage of the present invention, it has been found that a total dye concentration in the dual indicator reagent composition in the range of from about 0.5 mM to about 2mM is especially preferred. Furthermore, it also has been found that in addition to the citrate buffer used in the above example, the desired pH can be maintained at an essentially constant level by using any suitable buffer, such as malonate, lactate, trichloroacetate, sulfosalicylate, tartarate, phosphates, borates, acetates, piperazine-N,N'-bis(2-hydroxypropane)sulfonic acid (POPSO), N-2-hydroxyethylpiperazine-N'-2-ethanesulfonic acid (HEPES), 3-N-(tris-hydroxymethyl)methylamino-2-hydroxypropanesulfonic acid (TAPSO), 2-([tris-(hydroxymethyl)-methyl] amino)ethanesulfonic acid (TES), or other suitable buffers as are well known in the art.

Additionally, the two indicator dyes included in the dual indicator reagent composition do not necessarily have to be present in equal amounts. The relative amount of each dye depends upon a variety of parameters, including the intensity of the dye color transition and ability of the dye to interact with proteins. However, it has been found that a ratio of the first indicator dye to the second indicator dye within a range of from about 5 to 1 to about 1 to 5, and preferably in the range of from about 3 to 1 to about 1 to 3, provides the full advantages and benefits of the present invention.

Furthermore, in accordance with another important feature of the present invention, it is well within the experimental techniques of those skilled in the art of preparing test devices to design a system for the aqueous semi-quantitative assay of proteins in urine and other liquid samples by varying the relative amounts of aqueous solvent, dual indicator reagent composition, and urine sample, and by varying the identity and amount of dyes and buffer, to provide detectable and differentiable color transitions, such that a comparison, either visually and/or by instrument, to color standards derived from solutions of known protein concentration is possible.

In addition to the wet phase, aqueous assay for proteins, the dual indicator reagent composition can be used in dry phase, test pad assays for protein. The dry phase, test pad assay for protein that utilizes the dual indicator reagent composition is performed in accordance with methods well known in the art. In general, the assay for protein is performed by contacting the urine or other test sample with an analyte detection device that includes the dual indicator reagent composition. The analyte detection device can be dipped into the test sample, or the test sample can be applied to the analyte detection device dropwise. The resulting change in color of the analyte detection device demonstrates the presence of protein; and, if so designed, the resulting color transition can be compared to a standardized color chart to provide a semiquantitative measurement of the concentration of protein in the urine or test sample.

Typically, the analyte detection device is a reagent impregnated test strip, designed either as a single pad test strip (to assay only for a single analyte) or as a multiple pad test strip (to assay for several analytes simultaneously). For either type of reagent impregnated test strip, the test strip includes a support strip, or handle, normally constructed from a hydrophobic plastic, and a reagent test pad, comprising a bibulous or non-bibulous carrier matrix In general, the carrier matrix is an absorbent material that allows the test sample to move, in response to capillary forces, through the matrix to contact the indicator reagent composition and produce a detectable and measurable color transition.

The carrier matrix can be any substance capable of incorporating the chemical reagents required to perform the assay of interest, as long as the carrier matrix is substantially inert with respect to the chemical reagents, and is porous and/or absorbent relative to the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulosic beads, and especially fiber-containing papers such as filter paper or chromatographic paper; synthetic or modified naturally-occuring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. Hydrophobic and non-absorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix must include a hydrophilic or absorptive material. The handle usually is formed from hydrophobic materials such as cellulose acetate, polyethylene, terephthalate, polycarbonate or polystyrene, and the carrier matrix is most advantageously constructed from bibulous filter paper or nonbibulous polymeric films.

To achieve the full advantage of the present invention, the dual indicator reagent composition is impregnated into a suitable carrier matrix and utilized in a dry phase test strip for the assay of protein in a test sample. The method of the present invention affords an economical, accurate and reliable assay for the total concentration of protein in test samples that can be performed at home or in the laboratory. In addition, the method of the present invention allows detection, differentiation and measurement of low protein concentrations in the test sample therefore making the assay more useful clinically.

In accordance with the method of the present invention, to perform a dry phase, test strip assay for protein, a aqueous solution, including from about 0.5 mM to about 5 mM total concentration of the two indicator dyes methyl orange (MO) and bromophenol blue (BPB) first is prepared. A bibulous matrix, such as filter paper, then is saturated and impregnated with the aqueous solution containing the two dyes either by spreading, by immersing or by spraying the aqueous solution onto sheets or precut strips of the filter paper. After removing the aqueous solvent by oven drying in an air oven at about 50° C. for about 20 to 30 minutes, the filter paper then is saturated and impregnated with a 250 mM citrate buffer at pH 3.2 either by immersion or by spraying. After oven drying at about 50° C. for approximately 20 to 30 minutes, the filter paper impregnated with the dual indicator reagent composition is cut to an appropriate size, such as a pad having dimensions from about 0.25 cm by about 0.5 cm to about 0.5 cm by about 1.0 cm. Alternatively, it is sometimes possible to combine all the ingredients into one impregnating solution and therefore avoid the necessity of a two-dip impregnation procedure. The single dip procedure is especially recommended if the two dyes are sufficiently water soluble such that a second dip into the buffer solution could cause some of the dyes to leach out of the bibulous matrix.

The filter paper impregnated with the dual indicator reagent composition then is secured to an opaque or transparent hydrophobic plastic handle with double sided adhesive tape. The resulting test strip then was dipped into a fresh, uncentrifuged urine sample for a sufficient time to saturate the test pad with the sample. After waiting a predetermined time, such as 15 secs. to 60 secs., the test strip is examined, either visually or by instrument, for a response. The color transition, if any, of the test pad reveals the presence and/or concentration of protein in the urine sample.

Analogous to the aqueous, liquid phase assay for protein described above, it is well within the experimental techniques of those skilled in the art of preparing test devices to determine the proper balance between size of reagent pad, the strength of reagent impregnating solutions, the amount of test sample, and the method of introducing the test sample to the test strip, such as by pipetting rather than dipping, in order to design a semiquantitative assay for protein utilizing the method and composition the present invention.

In many cases simple visual observation of the test strip provides the desired information. If more accurate information is required, a color chart bearing color spots corresponding to various known protein concentrations, can be prepared for the particular dual indicator reagent composition used in the test strip. The resulting color of the test strip after contact with the urine sample then can be compared with the color spots on the chart to determine the protein concentration of the test sample.

If a still more accurate determination is required, a spectrophotometer or colorimeter can be used to more precisely determine the degree of color transition. In addition, both the aqueous, liquid phase assay and the dry phase, reagent strip assay can be made semiquantitative by employing spectrophotometric or colorimetric techniques, as opposed to visual techniques, in order to more reliably and more accurately measure the degree of color transition, and therefore more accurately measure the concentration of protein in the test sample, especially at lower protein concentrations, such as below 30 mg/dL.

As will be discussed more fully hereinafter in the detailed description of FIGS. 1 through 4, the ability to detect, differentiate between and measure low concentrations of proteins in a test sample by employing a dual indicator reagent composition surprisingly and unexpectedly provides a method of assaying for hard-to-detect low molecular weight proteins that may be present in the test sample. For example, the presence of low molecular weight Bence Jones proteins in urine is a diagnostic indication that the patient suffers from leukemia or multiple myeloma. However, according to present day methods, the detection of Bence Jones proteins in urine requires a heat and precipitation technique that is expensive and time-consuming. In addition, dry phase test strips have not been used to assay for Bence Jones proteins because the high molecular weight proteins in urine, such as albumin, interfere with and mask the Bence Jones proteins assay. The high molecular weight proteins in urine are present in considerably greater quantities than the Bence Jones proteins and therefore the high molecular weight proteins preferentially react with the indicator dye. Furthermore, separation of the Bence Jones proteins from the other protein constituents in urine is as expensive and time-consuming as the present day Bence Jones proteins assay, therefore making a protein separation step, prior to a dry phase test strip assay, a useless manipulative test. Accordingly, until the method of the present invention, no dry phase, test strip technique was available to accurately detect and measure the low concentrations of Bence Jones proteins usually found in urine.

Therefore, in accordance with an important feature of the present invention, it has been demonstrated that by impregnating the dual indicator reagent composition into a suitable carrier matrix, the presence and concentration of Bence Jones proteins in a urine sample can be achieved by using a dry phase test strip. Surprisingly and unexpectedly, the dry phase test strip assay of Bence Jones proteins is accomplished without separating the Bence Jones proteins from the sample, and without a masking of the Bence Jones proteins assay by the more abundant and interfering higher molecular weight proteins present in the urine. As previously discussed, a dry phase test strip used for the assay of proteins in test samples generally includes a carrier matrix comprising any absorbent matrix that is amenable to treatment and impregnation with an indicator reagent composition; that permits the urine or other test sample to permeate the carrier matrix rapidly enough to obtain protein assays relatively quickly; and that does not contaminate the urine or other test sample either by test sample extraction of components comprising the carrier matrix or by appreciably altering the urine or test sample in a way to make the subsequent assays inconclusive, inaccurate or doubtful.

If the test strip is designed to assay for the total protein content of a test sample, the carrier matrix can be any bibulous or non-bibulous material that allows permeation by the test sample to saturate the assay area of the test strip that is impregnated with the indicator reagent composition. To achieve the full advantage of the present invention, in the assay for the total protein content of a test sample, the carrier matrix is a hydrophilic, bibulous matrix, including cellulosic materials, such as paper, and preferably filter paper. Filter paper possesses all of the qualities required of a bibulous matrix of the present invention, plus the advantages of abundant supply, favorable economics, and a variety of suitable grades. Filter paper has been found to be extremely satisfactory for use as a matrix material for suspending and positioning both the indicator dyes and the buffers.

However, it has been found that in utilizing the dual indicator reagent composition in a method and device to determine the presence and/or concentration of low molecular weight proteins, such as Bence Jones proteins, in a test sample, the filter paper and cellulosic bibulous matrices are unsuitable. The filter paper bibulous matrix and related bibulous matrices possess sufficient porosity to allow the relatively high molecular weight proteins, such as albumin, to penetrate the bibulous matrix, and contact and interact with the impregnated dual indicator reagent composition to produce a color transition. Therefore, the proportionally large amount of relatively high molecular weight proteins present in the urine or other test sample precludes detection of the proportionally small amount of low molecular weight proteins present in the test sample. As a result, by incorporating the dual indicator reagent composition into a carrier matrix possessing a porosity that is sufficiently small to exclude the relatively high molecular weight proteins and simultaneously possessing a porosity that is sufficiently large to allow penetration by the low molecular weight proteins, provides a method of detecting and/or differentiating between the low levels of low molecular weight proteins in a test sample.

In accordance with an important feature of the present invention, it has been found that a polymerized urethane-based film, layer or membrane provides a carrier matrix having sufficient porosity to allow penetration of the low molecular weight proteins, such as Bence Jones proteins, and simultaneously to prevent penetration of the more abundant relatively high molecular weight proteins, such as albumin. As will be demonstrated in the embodiments of the present invention described hereinafter, the dual indicator reagent composition can be incorporated into a polymerized urethane-based film, layer or membrane either after forming the urethane-based film, layer or membrane or during the formation of the polymerized urethane-based film, layer or membrane. However, in either case, the polymerized urethane-based film, layer or membrane must be treated with a suitable buffer, if required, before the film, layer or membrane can be used in a device to detect proteins. Furthermore, the polymerized urethane-based film, layer or membrane must possess a suitable porosity to permit the detection and measurement of Bence Jones proteins in test samples. It should also be understood that polymerized urethane-based films, layers, or membranes can be produced that have a sufficiently high porosity to allow penetration by higher molecular weight proteins, like albumin, such that polymerized urethane-based films, layers or membranes can be used with the dual indicator reagent composition of the present invention to assay a liquid sample for total protein content.

It has been found that in order to provide a polymerized urethane-based film, layer or membrane of the appropriate porosity, a urethane compound, such as a urethane prepolymer, is included in an incompletely cured form as a component of a polymerizable urethane-containing composition. The polymerizable urethane compound is dispersed or dissolved in a liquid vehicle. The liquid vehicle, being removable from the dispersion or solution during curing of the polymerizable urethane-containing composition, allows the polymerizable urethane-containing compound to dry and cure as a continuous layer, film or membrane. The cured layer, film or membrane has the correct pore size to unexpectedly allow penetration of the relatively small, low molecular weight proteins and to exclude the relatively large high molecular weight proteins. The polymerized urethane-based film, layer or membrane is therefore suitable to function as the carrier matrix in a dry phase reagent test strip designed for the assay of Bence Jones proteins. The urethane compound dispersed or dissolved in the continuous liquid vehicle phase can be an oligomer, prepolymer, or incompletely cured polymer. The polymerizable urethane-containing composition can be mixed with the dual indicator reagent composition prior to curing, and the carrier matrix, including the dual indicator reagent composition, then is formed by curing the urethane-containing composition in layer form. The carrier matrix is cut into strips, then into pads, and secured to a plastic handle.

It has been found that the polymerizable urethane-containing composition, including a urethane compound like an oligomer, prepolymer, incompletely cured polymer or mixtures thereof that are capable of polymerization or further polymerization, form a cured film, layer or membrane when cured or polymerized upon removal of the continuous liquid vehicle phase during curing to provide a film, layer or membrane unexpectedly having sufficient permeability to low molecular weight proteins and essentially no permeability to relatively large molecular weight proteins. The urethane compound, after dissolving or dispersing in a continuous phase, such as by including an emulsifier, can be cured in any known manner. Further, the solution or dispersion of the urethane compound can include a suitable curing catalyst or can be heat cured so long as the solution or dispersion of the polymerizable urethane compound is applied as a layer in the form of an incompletely cured solution or dispersion. Generally, the urethane compounds that are useful in accordance with the present invention are those that can be dissolved or dispersed in a liquid vehicle, such as an organic solvent, like dimethylformamide, and are polymerizable in the dissolved or dispersed form to yield an essentially colorless and continuous film, layer or membrane upon curing.

In accordance with one embodiment of the present invention, the polymerizable urethane compound is a urethane prepolymer and particularly a urethane prepolymer comprising essentially repeating urethane units wherein the prepolymer chain is terminated at each end with isocyanate functionalities. It has been found that the urethane compound can be either neutral or cationic in character, or a combination of a neutral urethane compound and cationic urethane compound can be used. Examples of suitable commercial urethane prepolymers include DESMODERM KBH GRANULATE and DESMODERM KPK DISPERSION, both available commercially from BAYER AG.

The expression "urethane prepolymer" is understood to describe an essentially linear polymer of repeating urethane units. The urethane prepolymer has at least two isocyanate functionalities per molecule, and the polyurethane prepolymer should have a weight average molecular weight (Mw) of at least 50,000. Urethane prepolymers with weight average molecular weights below 50,000, for example down to about 30,000, also are useful so long as the prepolymers form a continuous film, layer or membrane upon curing. The maximum Mw is one wherein the urethane prepolymer can be solubilized or otherwise dispersed in a liquid vehicle or continuous phase, such as an organic solvent, like dimethylformamide. For the incompletely cured dispersed urethane prepolymer weight average molecular weights of up to about 500,000 are expected to be practical for the present invention. Upon curing, there is no upper limit to the molecular weight of the film layer or membrane. It has been found that to exercise the full advantages of the present invention the Mw for the polymerizable urethane prepolymer is within the Mw range of about 70,000 to about 80,000.

The urethane compound, such as a urethane prepolymer, useful in the method of the present invention can include other monomeric units that are incorporated into the urethane compound by copolymerizing an isocyanate containing monomer, hydroxyl containing monomer and a suitable third monomeric unit into the urethane prepolymer. Similarly, the polyurethane compound useful in the method of the present invention can be either neutral (DESMODERM KBH), anionic or cationic (DESMODERM KPK) in nature. More particularly, DESMODERM KBH is a neutral thermoplastic granular polymerized urethane material, obtained by reacting 75 parts of a polyester of adipic acid, including 70 mol % ethylene glycol and 30 mol % 1,4-butanediol ($M_w=2,000$); 25 parts of a polyester of adipic acid and 1,4-butanediol ($M_w=2,250$); 25 parts 1,4-butanediol; and 85 parts diphenylmethanediisocyanate. Cationic urethanes in general are formed by a reaction of a polyisocyanate, a polyol and a hydroxyl-containing tertiary amine, wherein the amine portion of the poly- urethane is subsequently neutralized with an organic acid, followed by dispersion of the neutralized polymerized urethane in water. Accordingly, DESMODERM KPK is a cationic, emulsifier-free polymerized urethane dispersion of a reaction product of 200 parts of a polyester of adipic acid, phthalic acid and ethylene glycol ($M_w=1,700$); 50 parts toluenediisocyanate; 20 parts N-methyldiethanolamine; and 6 parts p-xylylene dichloride.

In any event, the urethane compound utilized in the present invention, after mixing with the other components of the urethane-containing composition, must cure to produce a film, layer or membrane that has a physical and electrical charge structure that makes it permeable to low molecular weight proteins and impervious to relatively high molecular weight proteins. Furthermore, it should be understood that the urethane-containing composition can contain either a neutral urethane compound, a cationic urethane compound or a mixture of a neutral urethane compound and a cationic urethane compound. The urethane compound is present in the urethane-containing composition in a range of from about 3% by weight to about 30% by weight, and preferably from about 5% by weight to about 20% by weight, based upon the total weight of the urethane-containing composition.

As will be discussed more fully hereinafter, the percentage of urethane compound used in the urethane-containing composition, and the nature of the urethane compound, either neutral, cationic, or a neutral/cationic mixture, affects the degree of color resolution, the stability of color production, and the speed of color production. Therefore, in accordance with the method of the present invention, analyte test devices including a urethane-based carrier matrix can be designed for improved color resolution, increased color stability, or faster color production as required.

In addition to the polymerizable urethane compound, the polymerizable urethane-containing composition used to form the carrier matrix includes a dispersed inorganic phase, wherein the inorganic phase includes a water-insoluble inorganic compound, such as barium sulfate.

The urethane-containing composition includes from about 15% by weight to about 40% by weight, and preferably from about 20% by weight to about 30% by weight, based on the total weight of the urethane-containing composition, of a water-insoluble inorganic compound, such as barium sulfate, as a filler. The exact identity of the inorganic compound used as a filler is unimportant as long as the filler is white in color, so as not to interfere with color detection and measurement upon interaction of the indicator dyes and the protein; and as long as the inorganic filler is essentially water-insoluble, such that dissolved anions and/or cations are not available to interfere chemically or physically with the protein assay. Therefore, insoluble inorganic compounds that can be used in accordance with the method of the present invention include calcium sulfate, titanium dioxide, alumina, zinc oxide, magnesium oxide, calcium oxide, silicon dioxide, talc, magnesium aluminum oxide, magnesium titanium oxide, barium oxide, barium sulfate, strontium sulfate and other similar, white, water-insoluble inorganic compounds, especially oxides: or mixtures thereof.

The insoluble inorganic compound is incorporated into the urethane-containing composition as a powder to help assure uniform dispersion of the insoluble inorganic compound throughout the urethane-containing composition. In addition, by utilizing an insoluble inorganic compound in powder form, the insoluble inorganic compound is maintained uniformly dispersed throughout the urethane-containing composition during the curing process. The uniform dispersion of the insoluble inorganic compound provides a polymerized urethane-based film, layer or membrane having the insoluble inorganic compound uniformly dispersed throughout the film, layer or membrane.

The polymerizable urethane-containing composition also can include anionic surfactants to help wet the insoluble inorganic compound and therefore assist in homogeneously dispersing the insoluble inorganic compound throughout the urethane-containing composition. The anionic surfactants can be present from 0% by weight up to approximately 5% by weight, based on the total weight of the urethane-containing composition. The anionic surfactant may further act to help stabilize the color resulting from contact between protein and the dual indicator reagent composition. The anionic surfactants found useful in the method of the present invention are not necessarily limited to a particular type, and include ammonium, alkylammonium, potassium and/or sodium dodecylbenzene sulfonate, alkyl sulfonates, silylalkyl sulfonates, alkyl sulfates, alkyl ether sulfates, dioctyl sulfosuccinate, alpha olefin sulfonates, and alkyl sarcosinates; or mixtures thereof.

In addition, other surface active agents, such as silicon-containing materials, like a dimethylpolysiloxane fluid, can be incorporated into the urethane-containing composition in weight percentages of up to 2% based upon the total weight of the urethane-containing composition. These silicon-containing materials possess a low surface tension and therefore assist further in wetting the insoluble inorganic compound and also act to alter the surface tension of the urethane-containing composition to provide a leveling affect to produce smooth and "polished" films, layers or membranes of uniform thickness.

As discussed previously, the urethanecontaining composition also includes a liquid vehicle, like an organic solvent, capable of solubilizing and/or dispersing the urethane compound and any anionic surfactants or silicon-containing materials that may be present. The liquid vehicle also must be capable of dispersing the insoluble inorganic salt. The organic solvent must be relatively inert such that it will not react with the urethane compound and the solvent must evaporate at relatively low temperatures to provide a dry urethane-based film, layer or membrane. It has been demonstrated that organic aprotic solvents, such as dimethylformamide, N-methyl pyrrolidone, and dimethyl sulfoxide provide the required solvency to dissolve and disperse the components of the urethane-containing composition, provide the required inertness to preclude reaction of the solvent with the urethane compound, and possess the required vapor pressure to yield a solvent-free polymerized urethane-based film, layer or membrane. The liquid vehicle, removed during curing, is included in the urethane-containing composition in an amount of at least 30%, and preferably is present in an amount of at least 50% and up to about 90% by weight, based on the total weight of the polymerizable urethane-containing composition.

In accordance with one embodiment of the present invention, polymerizable urethane-containing compositions were mixed according to the formulations outlined in Example 1. The urethane-containing compositions A and B of Example 1, then were converted to urethane-based films, layers or membranes according to an identical curing method.

EXAMPLE 1

| Urethane-Containing Composition - A | |
|---|---|
| DESMODERM KBH (Neutral Urethane) | 7.3% |
| Sodium Dioctyl Sulfosuccinate | 0.2% |
| Barium Sulfate | 22.0% |
| Dimethylpolysiloxane Fluid | 1.4% |
| Sodium Dodecyl Benzenesulfonate | 1.4% |
| DESMODERM KPK (Cationic Urethane) | 10.0% |
| Dimethylformamide | 57.7% |
| Total | 100.0% |
| Urethane-Containing Composition - B | |
| DESMODERM KBH (Neutral Urethane) | 5.8% |
| Dralon U | 1.6% |
| Sodium Dodecyl Benzenesulfonate | 0.3% |
| Talc | 28.3% |
| Dimethylpolysiloxane Fluid | 0.1% |
| Dimethylformamide | 63.9% |
| Total | 100.0% |

Dralon U is a sulfonated polymer of average molecular weight of 48,000 and having the general structure illustrated in structural formula I.

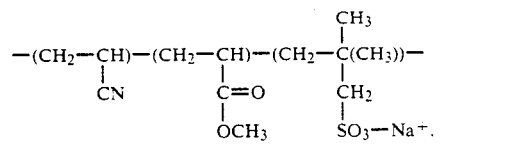

In the manufacture of both composition A and composition B of Example I, the components were thoroughly mixed using a high speed mixer until the composition was homogeneous.. To cure either the composition A or B into a film, layer or membrane, the composition is coated onto a transparent, impermeable plastic support. The thickness of the composition coating is controlled by using a doctor blade adjusted to a wet thickness of about 150 u to about 750 u. Immediately after coating the plastic support with the urethane-containing composition, the plastic support is immersed into a circulating water bath maintained at a constant temperature of about 25° C. to about 43° C. The urethane-containing composition is cured in the water bath by immersing the composition-coated support in the water bath for a time period ranging from 30 minutes to 16 hours. After curing, the film, layer or membrane can be air-dried or oven-dried. Reagents, such as a dual indicator reagent composition, then are impregnated into the dried film, layer or membrane as previously described. Alternatively, if the reagents comprising the dual indicator reagent composition are soluble in the organic solvent used in the manufacture of the urethane-containing composition, like dimethylformamide, and if the reagents comprising the dual indicator reagent composition are insoluble in water, the reagents can be incorporated into the urethane-containing composition and coated onto the support with the urethane-containing composition prior to curing.

To show the new and unexpected results arising from using the dual indicator reagent composition to detect and measure the amount of protein in a test sample, and to further show the surprising results arising from incorporating the dual indicator reagent composition into a urethane-based film, layer or membrane, especially in regard to the detection and measurement of low molecular weight proteins, like Bence Jones proteins, in a test sample, color space plots were made for total protein assays and for Bence Jones protein assays obtained from dry phase test strips including a single indicator impregnated into a filter paper bibulous matrix and into urethane-based carrier matrices and from impregnating a dual indicator reagent composition into a filter paper bibulous matrix and into polymerized urethane-based carrier matrices.

FIGS. 1-4 are color space plots obtained from contacting four standardized albumin solutions and from contacting a standardized solution of Bence Jones proteins with various dry phase test strips comprising either a single indicator dye or a dual indicator reagent composition impregnated into a carrier matrix comprising either filter paper or a polymerized urethane-based film, layer or membrane.

Figure 2:
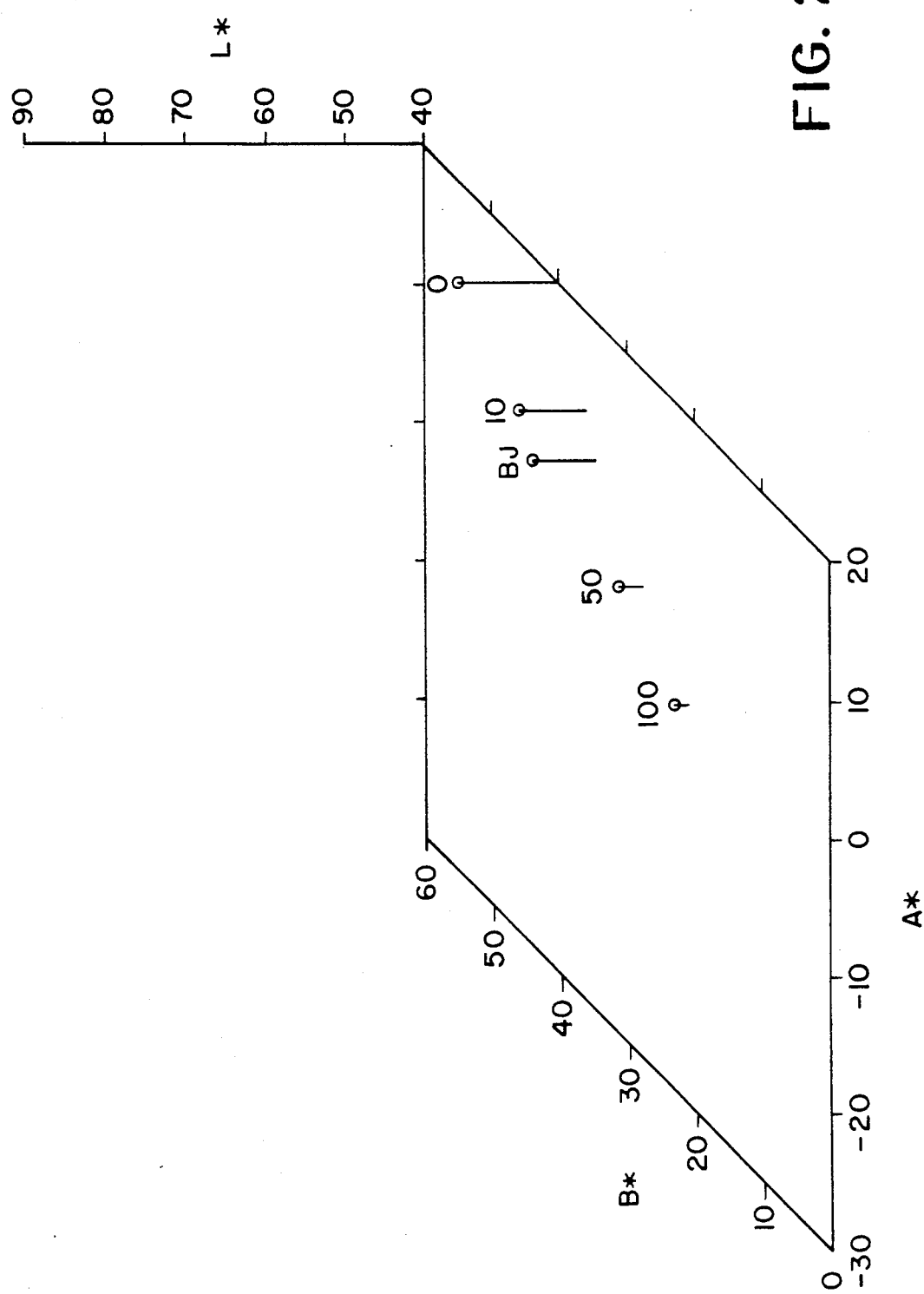
FIG. 2 is a color space plot showing the assay of liquid samples containing 0, 10, 50 and 100 mg/dL of albumin respectively and 100 mg/dL of Bence Jones proteins using a dry phase test strip comprising a filter paper bibulous matrix incorporating dual indicator dyes, tetrabromophenol blue (TBPB) and methyl orange (MO)
Figure 3:
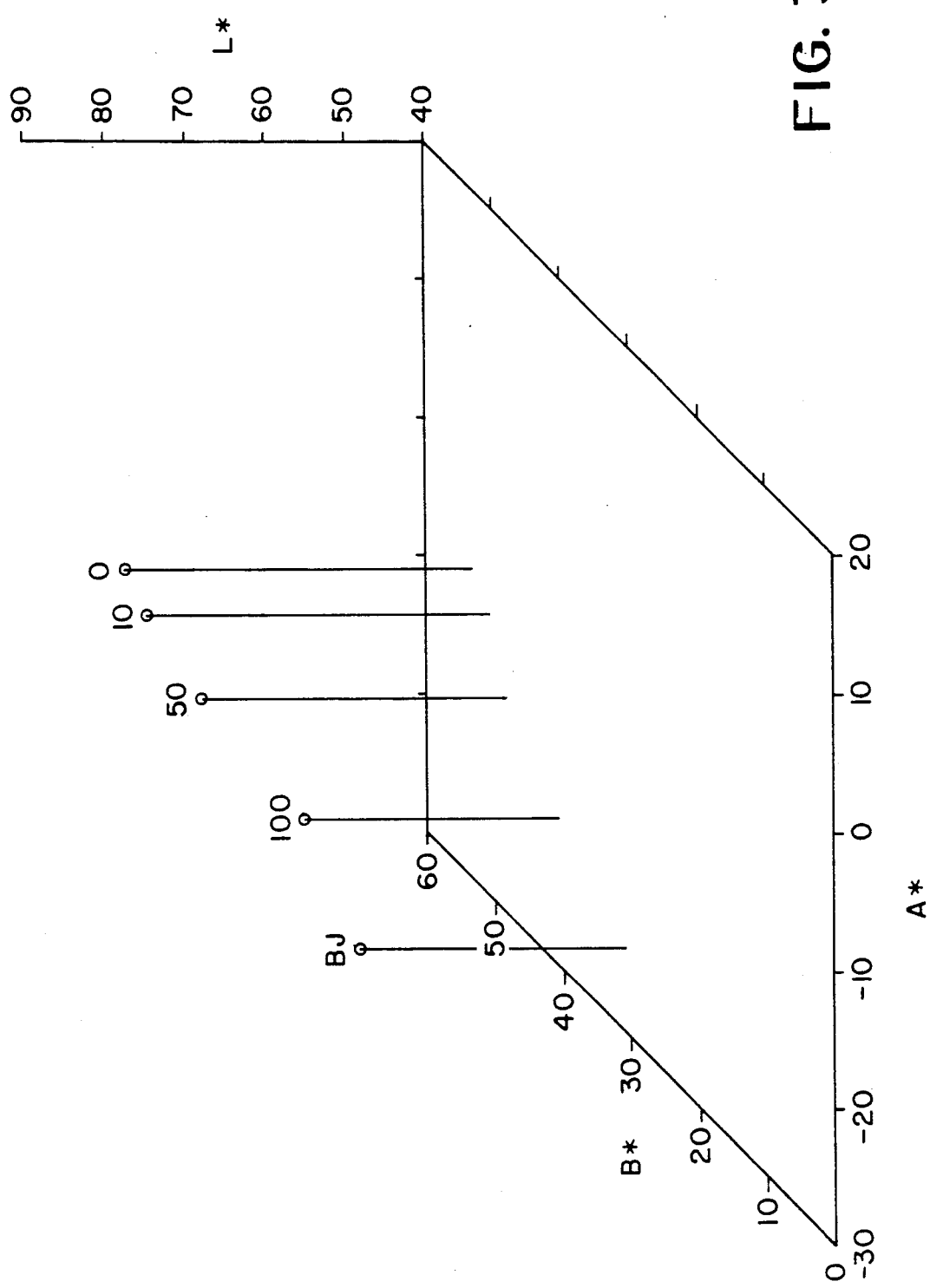
FIG. 3 is a color space plot showing the assay of liquid samples containing 0, 10, 50 and 100 mg/dL of albumin respectively and 100 mg/dL of Bence Jones proteins using a dry phase test strip comprising a carrier matrix comprising a polymerized urethane-containing film incorporating a single indicator dye, tetrabromophenol blue (TBPB)
Figure 4:
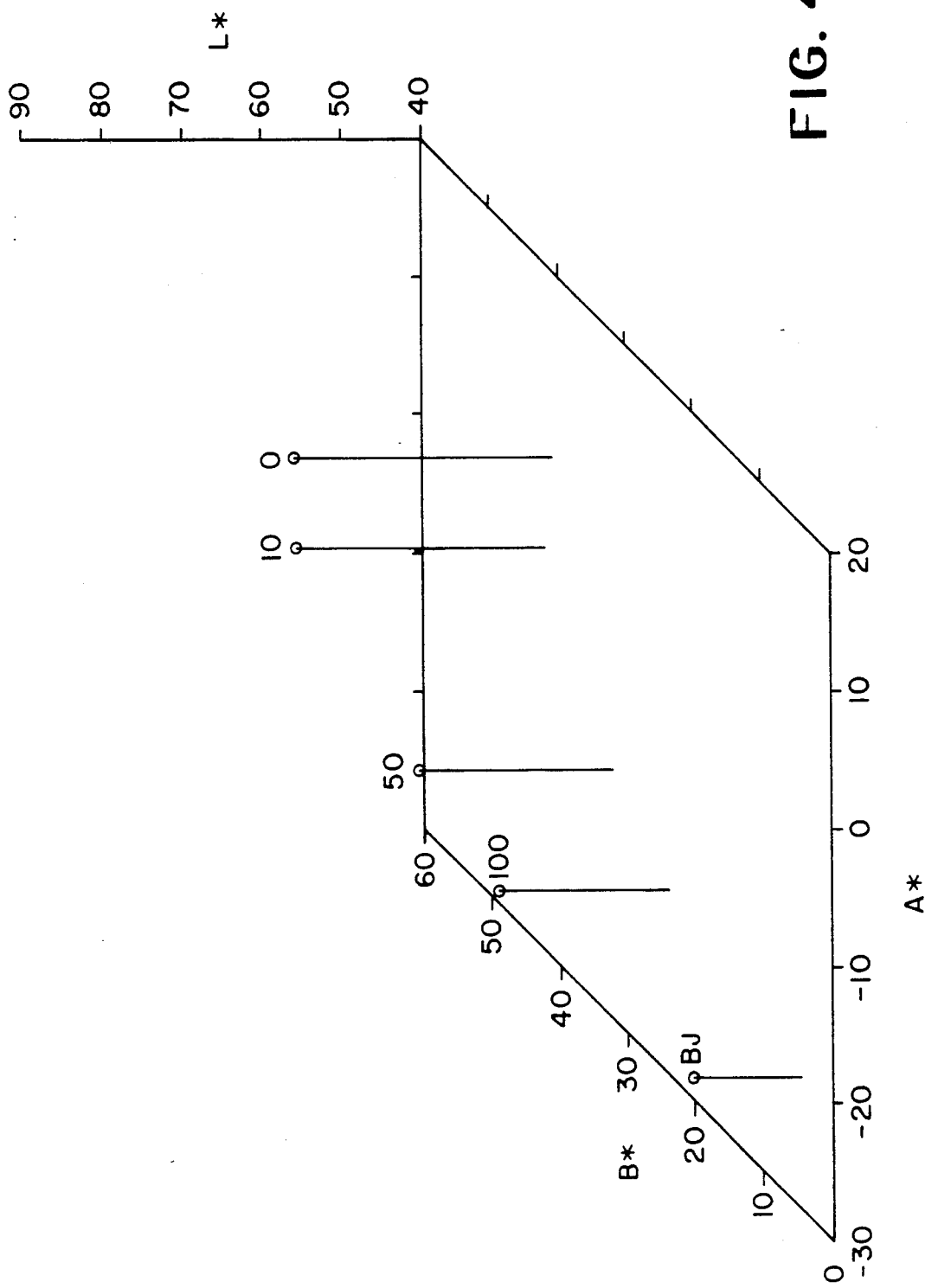
FIG. 4 is a color space plot showing the assay of liquid samples containing 0, 10, 50 and 100 mg/dL of albumin respectively and 100 mg/dL of Bence Jones proteins using a dry phase test strip comprising a carrier matrix comprising a polymerized urethane-containing film incorporating dual indicator dyes, tetrabromophenol blue (TBPB) and methyl orange (MO).

For example, FIG. 1 is the color space plot resulting from contacting a dry phase test strip comprising the single indicator tetrabromophenol blue (TBPB) impregnated into a filter paper carrier matrix with standardized solutions containing no albumin (0), 10 mg/dL albumin (10), 50 mg/dL albumin (50), 100 mg/dL albumin (100) and 100 mg/dL Bence Jones proteins (BJ). FIG. 2 is a color space plot for a dry phase test strip comprising a dual indicator reagent composition including tetrabromophenol blue (TBPB) and methyl orange (MO) impregnated into a filter paper carrier matrix that resulted from contacting the same standardized solutions of albumin and Bence Jones proteins. Similarly, FIG. 3 is a color space plot obtained from contacting the standardized protein solutions with a dry phase test strip comprising the single indicator tetrabromophenol blue (TBPB) incorporated into a polymerized urethane-based film obtained by curing composition A of Example 1. FIG. 4 is the color space plot obtained from contacting the standardized protein solutions with a dry phase test strip comprising a dual indicator reagent composition including tetrabromophenol blue (TBPB) and methyl orange (MO) incorporated into a polymerized urethane-based film obtained by curing composition B of Example 1.

As illustrated in FIGS. 1-4, a color space plot includes three axes, the $L^*$, $A^*$ and $B^*$ axes. The values of $L^*$ plotted on the vertical axis are a measure of the intensity of color, whereby a large $L^*$ value denotes a light color and $L^*=0$ denotes a completely black color. The horizontal $A^*$ axis is a measure of the color transition from green to red, whereby the more positive the $A^*$ value, the more red the color, and analogously, the more negative the $A^*$ value, the more green the color. Similarly, the third axis, $B^*$, is a measure of the color transition from blue to yellow, whereby the greater the value of $B^*$, the more yellow the color, and analogously the smaller the value of $B^*$, the more blue the color.

The color space difference ($\Delta E$) is calculated from the following equation:

$$\Delta E = \sqrt{(L_1^* - L_2^*)^2 + (A_1^* - A_2^*)^2 + (B_1^* - B_2^*)^2} \quad \text{Eq. 1}$$

wherein:

$L_1^*$, $A_1^*$, and $B_1^*$ are the color space values determined for a first standardized protein solution;

$L_2^*$, $A_2^*$ and $B_2^*$ are the color space values determined for a second standardized protein solution having a different protein concentration from the first standardized protein solution; and $\Delta E$ is the color space difference between the color space plots of the first and second standardized protein solutions.

The color space difference ($\Delta E$) is the straight line distance between two points in a three-dimensional color space plot. Theoretically, a color space difference of 1 is the smallest color difference the human eye can distinguish. However, because of the inherent differences between the visual capabilities of individuals, a color space difference ($\Delta E$) of about 5 is required in order to practically and confidently distinguish between colors.

The $L^*$, $A^*$ and $B^*$ values plotted on the color space plots of FIGS. 1 through 4 are calculated from the percent reflectance measurements taken at sixteen different wavelengths evenly spaced between 400 nm (nanometers) and 700 nm using standard equations well-known in the art. In general, the percent reflectance at each of the sixteen different wavelengths is multiplied by the intensity of the light at that wavelength. These values then are multiplied by standard weighing functions for the colors red, green and blue, and finally added together. These calculations yield three tristimulus values X, Y and Z, and $L^*$, $A^*$ and $B^*$ are calculated from the X, Y and Z tristimulus values using the following equations:

$$L^* = 116 \times [(Y/Y_o)^{\frac{1}{3}} - 16] \quad \text{(Eq. 2)}$$

$$A^* = 500 \times [(X/X_o)^{\frac{1}{3}} - (Y/Y_o)^{\frac{1}{3}}] \quad \text{Eq. 3}$$

$$B^* = 200 \times [(Y/Y_o)^{\frac{1}{3}} - (Z/Z_o)^{\frac{1}{3}}] \quad \text{Eq. 4}$$

wherein:

$X_o$, $Y_o$ and $Z_o$ are the tristimulus values for perfect white (i.e. reflectance $=100\%$ at all wavelengths), and X, Y and Z are the tristimulus values calculated as described above from the sixteen wavelengths between 400 nm and 700 nm.

From the color space plots of FIGS. 1 through 4, the color space differences ($\Delta E$) were calculated, and summarized in TABLE III. In interpreting TABLE III, the term, $\Delta E$(Alb 10-0) is the color space difference between protein assays for protein solutions containing 10 mg/dL of albumin and 0 mg/dL of albumin. Similarly, the term $\Delta E$(Alb50-0) is the color space difference between protein assays for protein solutions containing 50 mg/dL of protein and 0 mg/dL of protein. The terms $\Delta E$ (Alb100-0) and $\Delta E$ (BJ100-0) are analogously defined.

TABLE III

COLOR SPACE DIFFERENCES (ΔE) FOR SINGLE AND DUAL INDICATOR REAGENT SYSTEMS IN FILTER PAPER AND POLYMERIZED URETHANE-CONTAINING MATRICES

| FIG. NO. | CARRIER MATRIX | INDICATOR(S) | ΔE (Alb10-0) | ΔE (Alb50-0) | ΔE (Alb100-0) | ΔE (BJ100-0) |
|---|---|---|---|---|---|---|
| 1 | Filter Paper | Tetrabromophenol Blue | 4.8 | 19.2 | 25.5 | 4.4 |
| 2 | Filter Paper | Tetrabromophenol Blue and Methyl Orange | 9.1 | 22.0 | 30.2 | 12.2 |
| 3 | Urethane Composition A | Tetrabromophenol Blue | 3.2 | 9.9 | 20.6 | 29.3 |
| 4 | Urethane Composition B | Tetrabromophenol Blue and Methyl Orange | 7.1 | 21.6 | 30.4 | 48.9 |

0 = Albumin 0 mg/dL and Bence Jones protein 0 mg/dL
Alb10 = Albumin 10 mg/dL
Alb50 = Albumin 50 mg/dL
Alb100 = Albumin 100 mg/dL
BJ100 = Bence Jones proteins 100 mg/dL As illustrated in the color space plot of FIG. 1 and in TABLE III, protein assays were conducted on standardized solutions including albumin and Bence Jones proteins using a dry phase test strip having only a single indicator, tetrabromophenol blue, impregnated into a filter paper carrier matrix. From FIG. 1 and TABLE III, it is found that the color space difference between a solution containing 10 mg/dL of albumin and a solution containing no albumin is 4.8. Because the human eye can normally differentiate only between colors having a color space difference of approximately 5, this assay would be inconclusive as to whether the sample contained any albumin because the color differentiation between the test strip contacting the 0 mg/dL albumin solution and the test strip contacting the 10 mg/dL test strip could not be determined. At best, the assayer could estimate that the sample contained from 0 mg/dL albumin to about 10 mg/dL albumin.

Similarly, FIG. 1 and TABLE III demonstrate that an assayer could not determine the concentration of Bence Jones proteins in a test sample containing from 0 mg/dL of Bence Jones proteins to about 100 mg/dL of Bence Jones proteins because the color space difference provided by an analyte device having a single dye impregnated into a filter paper matrix is only 4.4, or a color space difference that is barely detectable by a normal human eye. TABLE III and FIG. 1 further show that the human eye can detect color differences resulting from the presence of 50 mg/dL and 100 mg/dL of albumin because the color space differences are 19.2 and 25.5, respectively.

However, surprisingly and unexpectedly, by impregnating a filter paper matrix with a dual indicator reagent composition of the present invention, an assayer can visually differentiate between samples containing 0 mg/dL of albumin and 10 mg/dL albumin. From FIG. 2 and TABLE III, a color space difference (ΔE) between a solution containing 10 mg/dL of albumin and a solution containing no albumin is 9.1 when using a dual indicator reagent composition including tetrabromophenol blue and methyl orange. Such a color space difference is sufficient to be discernible by the human eye, and shows a substantial improvement over the color space difference of 4.8 afforded by the single indicator dye of FIG. 1. Similarly, an assayer can visually detect Bence Jones proteins in a test sample because the color space difference between a 100 mg/dL solution of Bence Jones proteins and a 0 mg/dL solution of Bence Jones proteins is 12.2. Such a degree of color difference is sufficient to allow color differentiation by the human eye. Similarly, TABLE III and FIG. 2 shows enhanced color differentiation for the 50 mg/dL and 100 mg/dL albumin solutions compared to the solution containing no albumin.

In regard to FIG. 3, it is demonstrated that a single indicator dye impregnated into a polymerized urethane-based film, layer or matrix does not provide a method to determine the presence and/or concentration of low levels of albumin in a test sample. For a solution containing 10 mg/dL of albumin, the color space difference (ΔE) compared to a control solution containing 0 mg/dL albumin was only 3.2. This color space difference is insufficient for differentiation by the human eye. However, it is surprising that the polymerized urethane-based film matrix provided dramatically increased sensitivity in regard to Bence Jones proteins as the color space difference in FIG. 3 rose to 29.3 compared to the ΔE in FIG. 1 of 4.4 wherein a filter paper matrix was used.

Unexpectedly, even greater sensitivity in regard to Bence Jones proteins assay was found in FIG. 4, wherein a dual indicator reagent composition was incorporated into a polymerized urethane-based film matrix. Compared to FIG. 3, the color space index increased from 29.3 to 48.9 showing an unexpected increase in color resolution and sensitivity towards Bence Jones proteins. FIG. 4 further shows the benefits of using a dual indicator reagent composition incorporated into a polymerized urethane-based film matrix to assay for albumin because the ΔE value increased to the visually perceptible level of 7.1 for a solution containing 10 mg/dL of albumin compared to the visually imperceptible ΔE value of 3.2 from FIG. 3, wherein a single indicator dye was utilized.

Overall, FIGS. 1-4 and TABLE III shows that a dual indicator reagent composition impregnated into a filter paper matrix or into a polymerized urethane-based film matrix improves color resolution and assay sensitivity in the assay for the total protein content of a liquid test sample, especially at low protein levels of less than 30 mg/dL. The method and composition of the present invention allow visual differentiation of color transitions resulting from contact of the reagent-containing carrier matrix with a test sample containing protein at levels of between 0 mg/dL and 10 mg/dL, thereby providing more accurate and trustworthy assays. The present invention further provides a method to quickly and accurately test for Bence Jones proteins, and other low molecular weight proteins, in a test sample by providing a carrier matrix that essentially removes interfering high molecular proteins and by providing a reagent composition of sufficient sensitivity to allow detection and measurement of low concentrations of low molecular weight proteins.

It has been demonstrated that color differences are improved by using the dual indicator reagent composition, regardless of whether the carrier matrix is filter paper or a polymerized urethane-based film, membrane or layer. In addition, employing the dual indicator reagent composition in a polymerized urethane-based film matrix shows dramatically increased sensitivity to low molecular weight proteins therefore providing a simple dry phase test strip procedure to assay for low molecular weight proteins. As demonstrated in FIGS. 1-4 and in TABLE III, assaying a solution containing 100 mg/dL of Bence Jones proteins with a single indicator dye incorporated into a filter paper matrix gave an imperceptible color difference of 4.4 compared to assaying a solution containing no Bence Jones proteins. However, color resolution and assay sensitivity is improved by incorporating the same single dye into a polymerized urethane-containing matrix such that the color difference is an easily perceptible 29.3. Furthermore, using the dual indicator reagent composition incorporated into a polymerized urethane-based film matrix further dramatically improves the color resolution and assay sensitivity such that the color difference increases to an unexpected level of 48.9.

In regard to using a polymerized urethane-based film, layer or membrane as the carrier matrix for a dual indicator reagent composition in the assay for low molecular weight proteins, it has been found that not all urethane-based membranes respond identically to contact with protein-containing solutions, and therefore, several urethane-based film matrices are unsuitable because of high blank color development, insufficient color differentiation between protein levels and/or color leaching into aqueous phase. It has been shown that the two polymerized urethane-based film matrices obtained by curing composition A or composition B of Example 1 do not demonstrate these disadvantages and therefore are preferred. It should be emphasized however that compositions A and B are not the only compositions that can be utilized according to the method of the present invention as matrices to provide good protein determinations.

Nevertheless, a membrane, layer or film obtained by curing either composition A or by curing composition B of Example 1 has advantages and disadvantages. For example, a membrane or film obtained by curing composition A of Example 1 gives excellent color differentiation and excellent color stability even after the test sample is wiped dry from the membrane. For example, for analyte test devices using membranes or films derived from curing composition A of Example 1, the color transition resulting from contact with albumin or Bence Jones proteins showed no visual deterioration in color intensity or depth over a several day period. However, color formation in films derived from composition A is slow, and therefore this film may have limitations if used in the usual dip-and-read manner. As a result, when using the film matrix derived from composition A, the test sample is pipetted onto the film matrix and allowed to contact the film matrix for approximately 2 minutes. The color generated in response to the albumin contact then is determined either visually or instrumentally and either with the test sample remaining in contact with the matrix or after the sample is wiped from the matrix.

A urethane-based film matrix obtained by curing composition B of Example 1 also offers very good color resolution and differentiation. However, unlike a carrier matrix formed by curing composition A of Example 1, color formation on a film matrix obtained by curing composition B of Example 1 is fast, and therefore, this film matrix can be used in the usual dip-and-read format in the assay for albumin. However, in the assay for Bence-Jones proteins color development is slow, in that 2 minutes is required for full color development. Therefore, the test strip would have to remain dipped in the urine sample for a relatively long time to generate a color transition. This disadvantage is overcome by pipetting the urine sample onto a test pad and allowing a 2 minute response time before examining the test strip for a response. Furthermore, after the sample is wiped off the matrix, the color generated in response to the protein content begins to fade, and therefore the degree and depth of color transition must be determined immediately after removing the liquid test sample from the test strip.

Therefore, in accordance with an important feature of the present invention, more accurate and reliable assays for total protein content, or for low molecular weight protein content, in urine and other liquid test samples can be performed by utilizing a dual indicator reagent composition. The dual indicator reagent composition improves the color resolution of the assay and therefore improves assay sensitivity, especially at low albumin levels of approximately 30 mg/dL and below. Furthermore, by performing the assay with a dry phase test strip that includes a polymerized urethane-based membrane, film or layer as the carrier matrix for the dual indicator reagent composition, a new and unexpectedly accurate method of determining the presence and/or concentration of low molecular weight proteins, like Bence Jones proteins, in the test sample is provided.

Obviously, many modifications and variations of the invention as hereinbefore set forth can be made without departing from the spirit and scope thereof and therefore only such limitations should be imposed as are indicated by the appended claims.

I claim:

1. A composition capable of exhibiting a sufficient color transition upon contacting a protein-containing liquid test sample to show the presence and/or concentration of protein in the liquid test sample comprising:

a first indicator dye capable of undergoing a detectable and measurable color transition from a first color to a second color;

a second indicator dye capable of undergoing a detectable and measurable color transition at approximately the same pH as the first indicator dye to a color that differs form the second color of the first indicator dye; and a suitable buffer to maintain a constant pH sufficiently close to the color transition pH of the first indicator dye and the color transition pH of the second indocator dye, wherein each dye is capable of preferentially interacting with protein in the test sample to undergo any said color transition, wherein any said color transitions of the dyes no not mutually interfere with each other, and wherein each of the dyes have approximately the same affinity for protein in the test sample.

2. The composition of claim 1 wherein the first indicator dye undergoes a color transition from a less intense color to a more intense color.

3. The composition of claim 1 wherein the weight ratio of the first indicator dye to the second indicator dye is in the range of approximately 5 to 1 to approximately 1 to 5.

4. The composition of claim 3 wherein the weight ratio of the first indicator dye to the second indicator dye is in the range of approximately 3 to 1 to approximately 1 to 3.

5. The composition of claim, wherein the first indicator dye and the second indicator dye exhibit a color transition at an acidic pH.

6. The composition of claim 5 wherein the acidic pH is maintained constant by adder buffer selected from the group consisting of citrate, malonate, lactate, trichloroacetate, sulfosalicylate, tartarate, phosphates, borates, acetates, piperazine-N,N'-bis(2-hydroxypropane)sulfonic acid (POPSO), N-2-hydroxythylpiperazine-N'-2-ethanesulfonic acid (HEPES), 3-N-(trishydroxymethyl)methylamino-2-hydroxypropanesulfonic acid (TAPSO), and 2-([atris-(hydroxymethyl)methyl] amino)ethanesulfonic acid (TES); or combinations thereof.

7. The composition of claim 5 wherein the first indicator dye and the second indicator dye exhibit a color transition at a pH of approximately 5 or less.

8. The composition of claim 7 wherein the color transition pH of the first indicator dye and the color transition pH of the second indicator dye differ by approximately 0.2 pH unit or less.

9. The composition of claim 1 wherein the color transition pH of the first indicator dye and the color transition pH of the second indicator dye differ by approximately 0.5 pH unit or less.

10. The composition of claim 1 wherein the first indicator dye and the second indicator dye are selected from the group consisting of bromochlorophenol blue, iodophenol blue, rose bengal, bromophenol blue, methyl orange, tetrabromophenol blue, bromopyrogallol red, bromocresol green, tetrabromophenolphthalein ethyl ester, bromophenol red, 8-amino-11-aza-6-thia-[5,12-naphthacenequinone] and bromocresol purple.

11. The composition of claim 1 wherein the first indicator dye is selected from the group consisting of bromochlorophenol blue, iodophenol blue, rose bengal, bromophenol blue, tetrabromophenol blue, bromopyrogallol red, bromocresol green, tetrabromophenolphthalein ethyl ester, bromophenol red, 8-amino-11-aza-6-thia-[5,12-naphthacenequinone] and bromocresol purple.

12. The composition of claim 1 wherein the second indicator dye is selected from the group consisting of methyl orange and bromophenol red.

13. The composition of claim 1, wherein the first indicator dye is selected from the group consisting of bromochlorophenol blue, bromophenol blue, tetrabromophenol blue, and iodophenol blue and the second indicator dye is methyl orange.

14. The composition of claim 1 wherein the first indicator dye is 8-amino-11-aza-6-thia-[5,12-naphthacenequinone], and the second indicator dye is bromophenol red.

15. The composition of claim 1 wherein the first indicator dye is bromocresol green and the second indicator dye is bromophenol red.

16. An analyte detection device for determining the presence and/or concentration of protein in a liquid test sample comprising:
a support strip;
a reagent test pad attached to said support strip; and
a dual indicator reagent composition incorporated into the reagent test pad, said dual indicator reagent composition comprising:
a first indicator dye capable of undergoing a detectable and measurable color transition from a first color to a second color;
a second indicator dye capable of undergoing a detectable and measurable color transition at approximately the same pH as the first indicator dye to a color that differs from the second color of the first indicator dye; and
a suitable buffer to maintain a constant pH sufficiently close to the color transition pH of the first indicator dye and the color transition pH of the second indicator dye,
wherein each dye is capable of preferentially interacting with protein in the test sample to undergo any said color transition, wherein any said color transitions of the dyes do not mutually interfere with each other, and wherein each of the dyes have approximately the same affinity for protein in the test sample.

17. The analyte detection device of claim 16 to determine the presence and/or concentration of albumin in a liquid test sample wherein the reagent test pad comprises either a bibulous matrix or a nonbibulous matrix. the reagent test pad comprises either a bibulous matrix or a nonbibulous matrix.

18. The analyte detection device of claim 17 wherein the bibulous matrix is filter paper or the nonbibulous matrix is a polymerized urethane-based film, layer or membrane.

19. The analyte detection device of claim 16 for determining the presence and/or concentration of Bence Jones proteins in a liquid sample wherein the reagent test pad comprises a nonbibulous matrix.

20. The analyte detection device of claim 19 wherein the nonbibulous matrix is a polymerized urethane-based film, layer or membrane.

21. A test article for detecting the relative concentration of a protein i a test fluid comprising a matrix layer polymerized from a polymerizable urethane compound dispersed in a liquid vehicle and having homogeneously incorporated therein a dual indicator reagent composition capable of reaction with said protein of said test fluid, said reaction being one producing a detectable change in said matrix, and wherein
(a) said matrix is permeable to said protein, and
(b) the dual indicator reagent composition comprises a first indicator dye capable of undergoing a detectable and measurable color transition from a first color to a second color;
a second indicator dye capable of undergoing a detectable and measurable color transition at approximately the same pH as the first indicator dye to a color that differs from the second color of the first indicator dye; and
a suitable buffer to maintain a constant pH sufficiently close to the color transition pH of the first indicator dye and the color transition pH of the second indicator dye, and
wherein each dye is capable of preferentially interacting with protein in the test sample to undergo any said color transition, wherein any said color transitions of the dyes do not mutually interfere with each other, and wherein each of the dyes have approximately the same affinity for protein in the test sample.

* * * * *